(12) United States Patent
Kobayashi

(10) Patent No.: US 6,256,091 B1
(45) Date of Patent: Jul. 3, 2001

(54) TRANSPARENT SUBSTRATE MOUNTING PLATFORM, TRANSPARENT SUBSTRATE SCRATCH INSPECTION DEVICE, TRANSPARENT SUBSTRATE BEVELLING INSPECTION METHOD AND DEVICE, AND TRANSPARENT SUBSTRATE INSPECTION METHOD

(75) Inventor: Ryo Kobayashi, Tokyo (JP)

(73) Assignee: Nippon Maxis Co., Ltd., Tokyo (JP)

( * ) Notice: Subject to any disclaimer, the term of this patent is extended or adjusted under 35 U.S.C. 154(b) by 0 days.

(21) Appl. No.: 09/134,359

(22) Filed: Aug. 14, 1998

(30) Foreign Application Priority Data

Aug. 25, 1997 (JP) .................................. 9-227920
Feb. 18, 1998 (JP) ................................. 10-036318
Feb. 18, 1998 (JP) ................................. 10-036340

(51) Int. Cl.$^7$ ................................. G01N 21/00
(52) U.S. Cl. ...................... 356/237.1; 356/239; 356/382
(58) Field of Search ..................... 356/237.1, 239, 356/382

(56) References Cited

U.S. PATENT DOCUMENTS 5,530,237 * 6/1996 Sato et al. ...................... 250/201.4
5,907,396 * 5/1999 Komatsu et al. ................ 356/237.1

FOREIGN PATENT DOCUMENTS

| | | |
|---|---|---|
| 64-40054 | 3/1989 | (JP) . |
| 4-107946 | 4/1992 | (JP) . |
| 5-134393 | 5/1993 | (JP) . |
| 7-27714 | 1/1995 | (JP) . |
| 7-103905 | 4/1995 | (JP) . |
| 7-159337 | 6/1995 | (JP) . |
| 8-145895 | 6/1996 | (JP) . |
| 8-285789 | 11/1996 | (JP) . |
| 9-288063 | 11/1997 | (JP) . |

* cited by examiner

Primary Examiner—Frank G. Font
Assistant Examiner—Reginald A. Ratliff
(74) Attorney, Agent, or Firm—Oliff & Berridge, PLC

(57) ABSTRACT

When mounting crystal blanks, crystal blanks can be mounted readily in a desired position on a mounting platform, and during pick-up, they can be readily detached from the mounting platform.

To inspect scratches in a crystal blank 1, diffused oblique light is shined onto the crystal blank 1 from below by light-emitting diodes 6, and light reflected by scratches on the crystal blank 1 is detected by image capturing means 11 directly above the crystal blank 1. The crystal blank 1 is conveyed to the mounting platform 2 by a conveyor robot arm 15, and after inspection, it is conveyed away by same. A plurality of grooves are formed in the mounting surface 3 of the mounting platform 2. Thereby, during mounting, the crystal blank 1 does not slide over the mounting platform 2 and after mounting, it does not adhere tightly to the mounting platform 2.

19 Claims, 23 Drawing Sheets

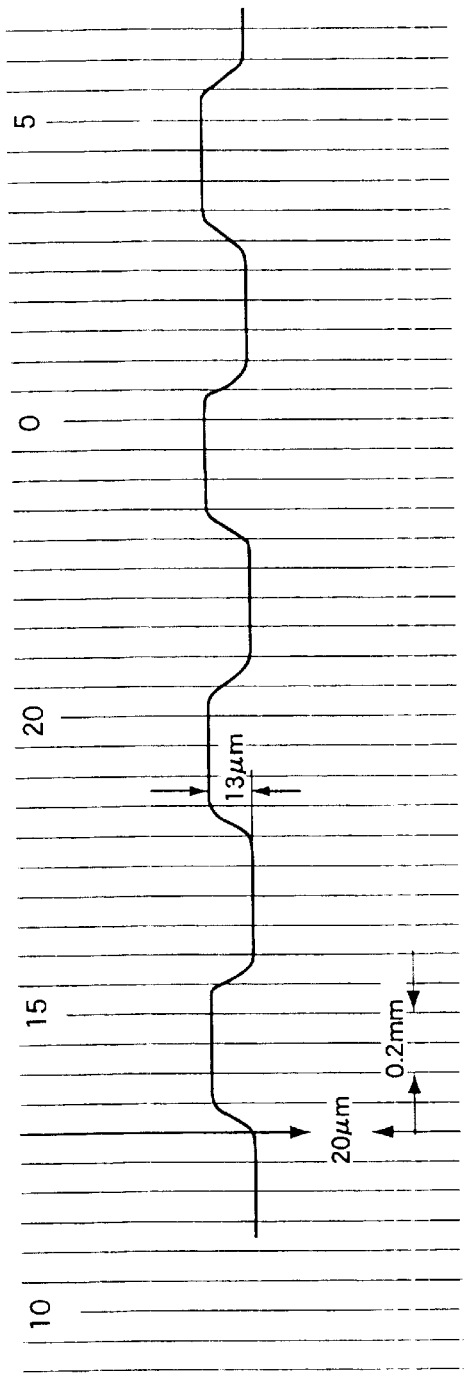
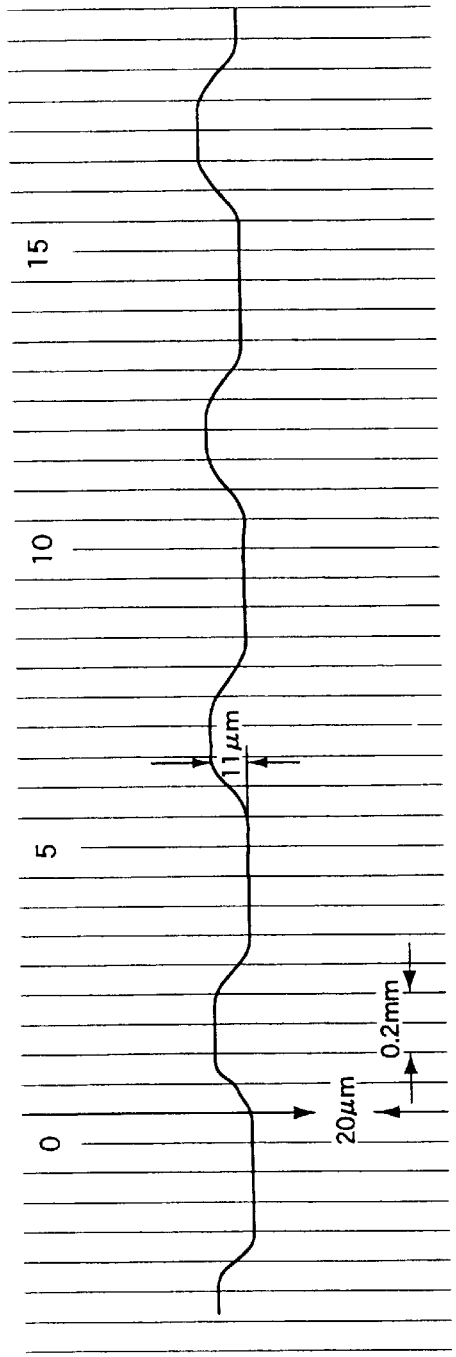

FIG.7(a) 0.5H
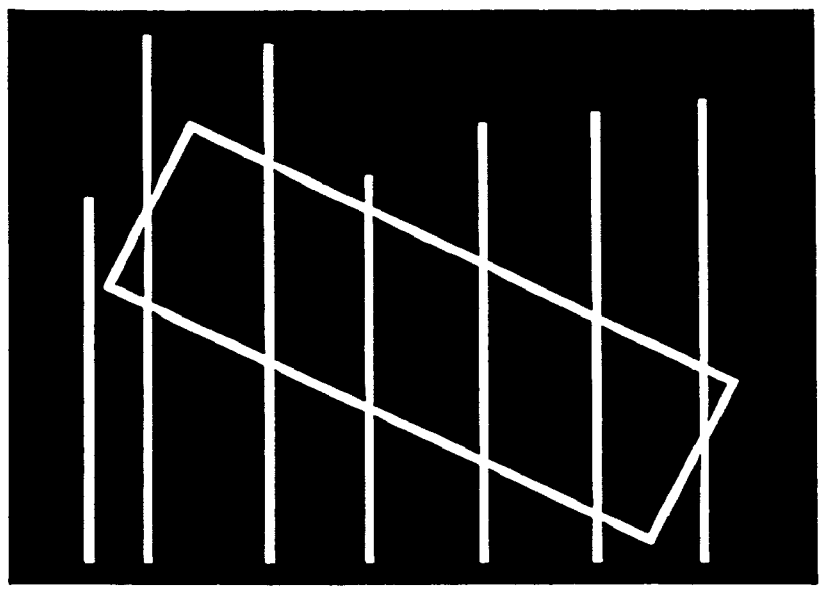
FIG.7(b) 1.0H
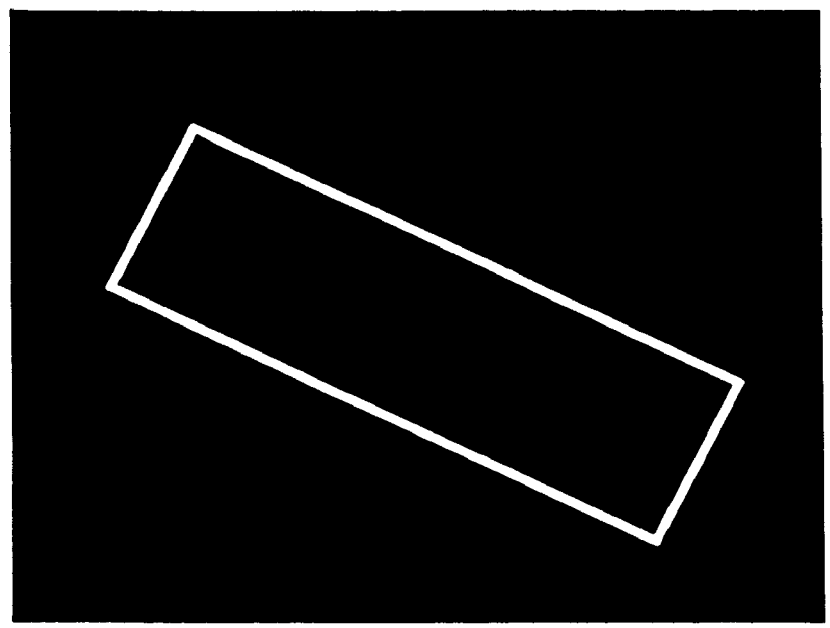

FIG.13(a) IMAGE BEFORE DIGITIZATION
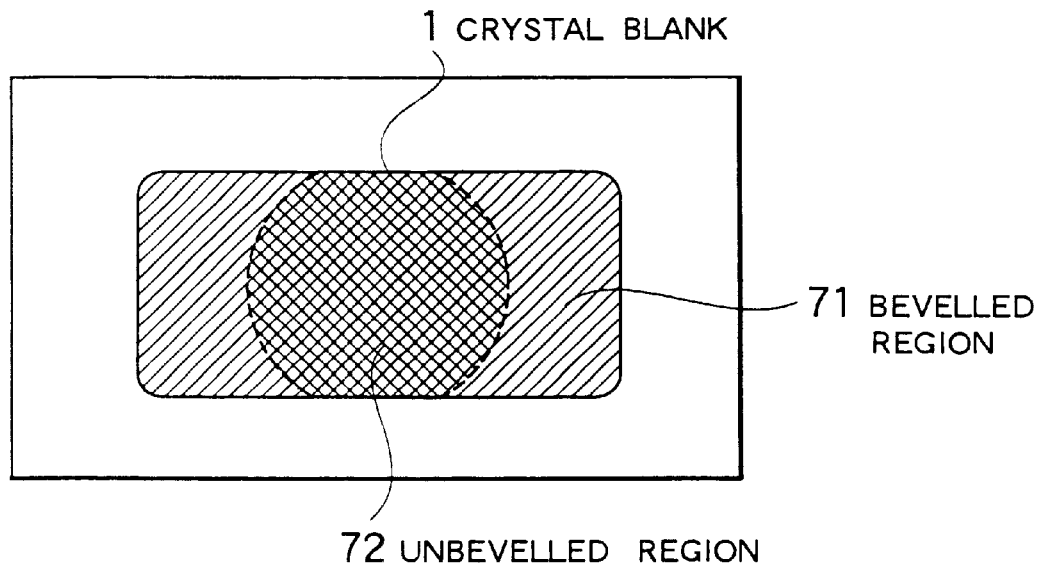
1 CRYSTAL BLANK
71 BEVELLED REGION
72 UNBEVELLED REGION
FIG.13(b) IMAGE AFTOR DIGITIZATION
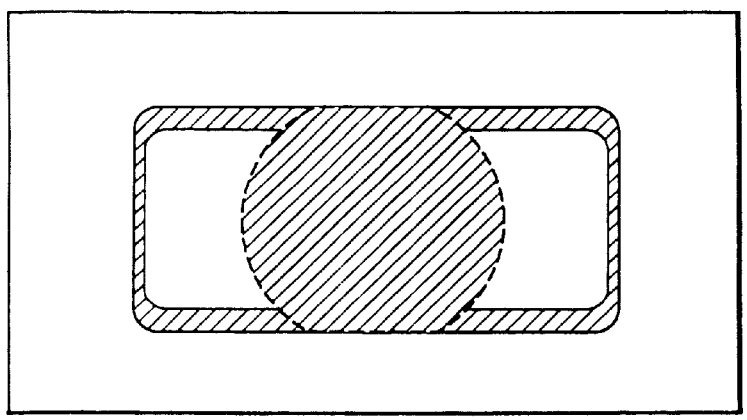

71
72

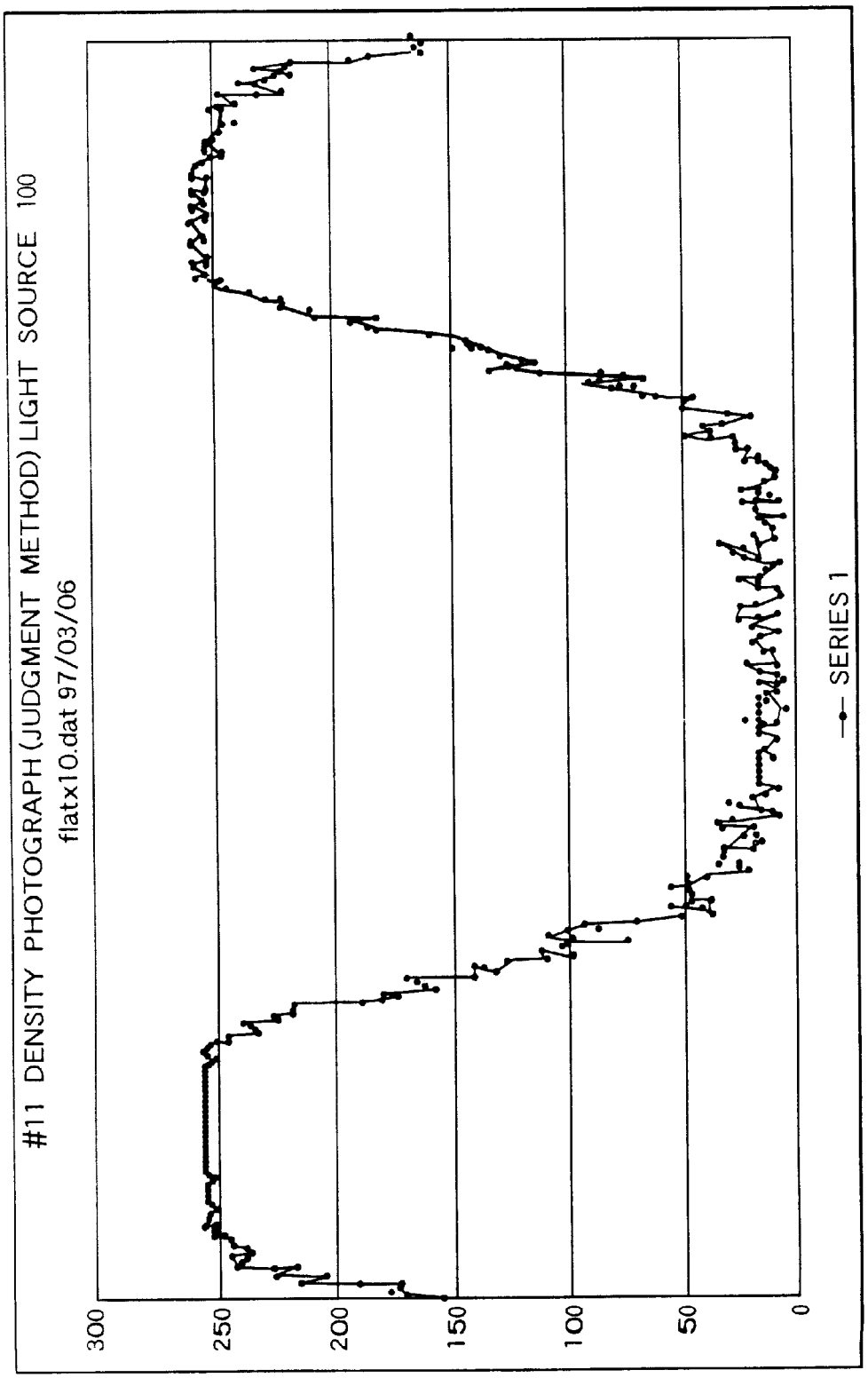

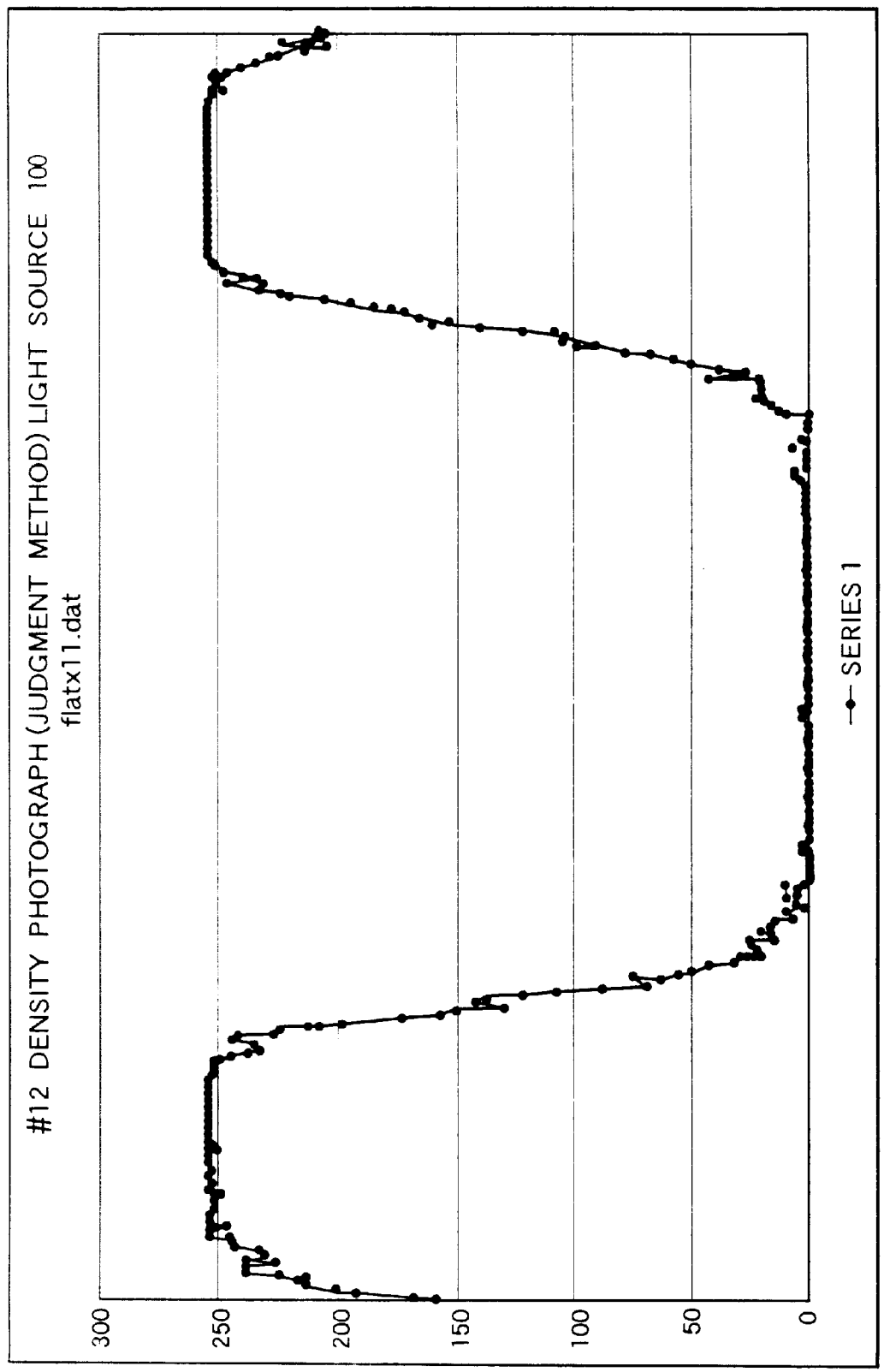

FIG.21

CRYSTAL SCRATCH INSPECTION

| RUN | OPERATING DATA | PARAMETERS | CATEGORY | CAMERA ADJUSTMENT | UTILITY |

SET FILE
PARAMETER FILE NAME : test1216beve.PA

[INPUT] [SAVE] [PRINT]

SHAPE SECTION
◉ STRIP  ○ CIRCULAR  ○ BEVEL

REGIONS A,B SHORTER EDGE DIMENSION
A [0.1] mm   B [0.05] mm

☐ REGION A
▦ REGION B
☐ REGION C
▨ REGION D (FLAT SECTION)

EXTERNAL DIMENSION AND FLAT SECTION DIMENSIONS
LONGER EDGE     [4.921] ± [0.006] mm
SHORTER EDGE    [2.085] ± [0.009] mm
R(CORNER)       [0.066] ± [0.100] mm
FLAT LONGER EDGE [0.714] ± [0.020] mm
FLAT SHORTER EDGE [2.085] ± [1.043] mm
LENTRE DIVERGENCE        ± [0.100] mm

JUDGEMENT LEVEL AND SCRATCH SURFACE AREA
A(LONGER)LEVEL      [100]   A SCRATCH SURFACE AREA [10]
B(SHORTER)LEVEL     [100]   B SCRATCH SURFACE AREA [10]
C(INTERNAL)LEVEL    [105]   C SCRATCH SURFACE AREA [10]
D(FOUR CORNER)LEVEL [87]    D SCRATCH SURFACE AREA [10]

DISTRIBUTION TYPE  A [52]  B [27]  C [42]

[PARAMETER AUTOSET]   [INPUT PARAMETERS(F8)]   [END(F10)]

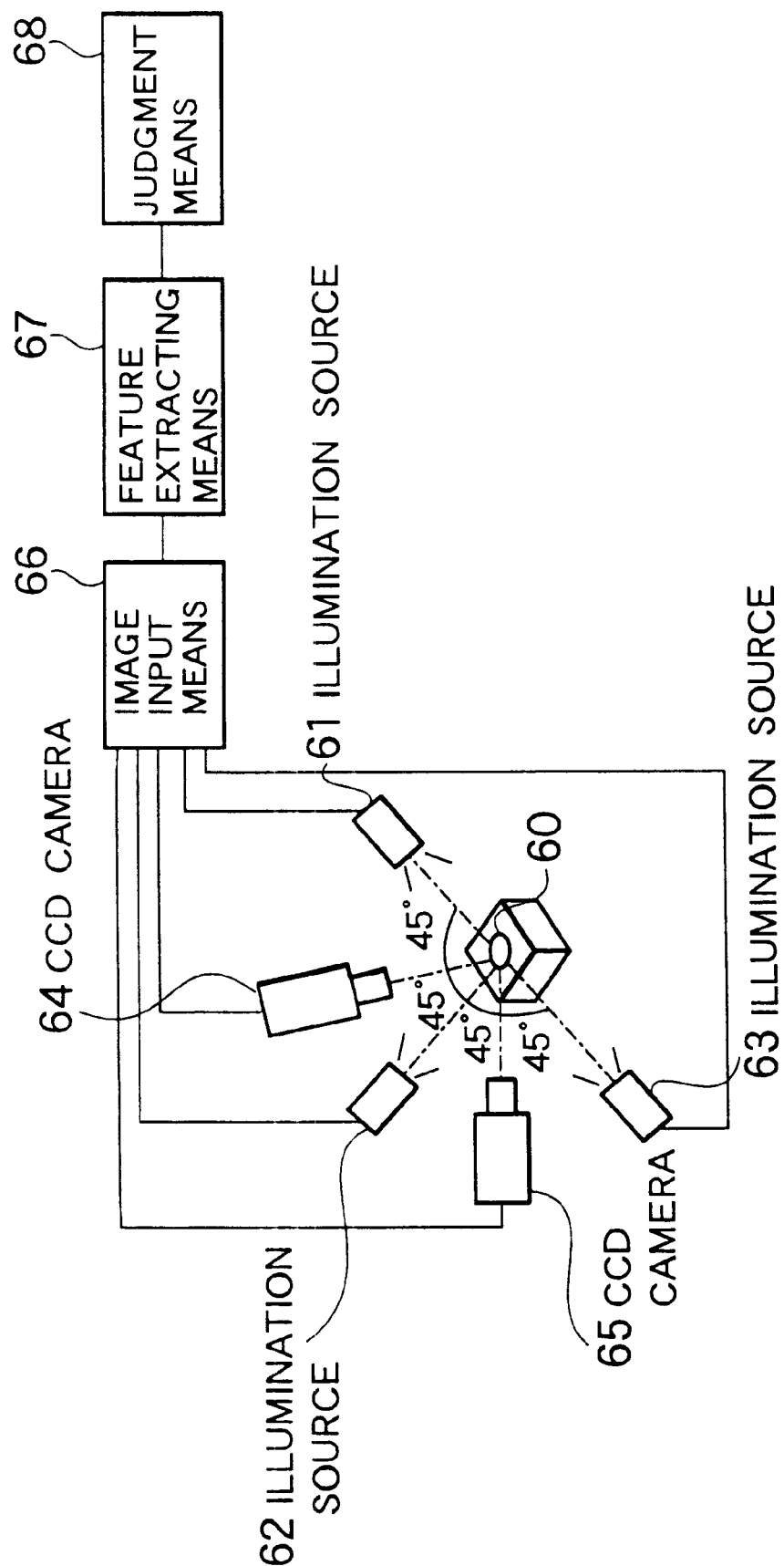

TRANSPARENT SUBSTRATE MOUNTING PLATFORM, TRANSPARENT SUBSTRATE SCRATCH INSPECTION DEVICE, TRANSPARENT SUBSTRATE BEVELLING INSPECTION METHOD AND DEVICE, AND TRANSPARENT SUBSTRATE INSPECTION METHOD

BACKGROUND OF THE INVENTION

1. Field of the Invention

The present invention relates to a crystal substrate mounting platform for mounting a crystal substrate, such as a crystal blank, and a scratch inspection device for crystal substrates for detecting scratches optically by mounting a crystal substrate on a the mounting platform, and more particularly, it relates to a crystal substrate mounting platform and crystal substrate scratch inspecting device whereby the handling of crystal substrates can be simplified. Furthermore, the present invention relates to a bevelling inspection method and device for crystal substrates, and more particularly, to a bevelling inspection method and device for crystal substrates whereby real-time inspection is possible by means of image processing. Moreover, the present invention relates to an inspection method for crystal substrates, and more particularly, to a method whereby scratches and the bevelling state of crystal substrates can be inspected region by region.

2. Description of the Related Art

Crystal oscillators are fabricated from crystal blanks, but if there is even the slightest scratch in the crystal blank, then the crystal oscillator will be defective, and therefore scratch detection in crystal blanks is extremely important.

Until now, defects in crystal blanks have been inspected visually by people, by since this operation depends on human sight, it is extremely difficult to detect scratches of the order of several ten μm or less. Moreover, since this operation continues for a long period of time, the operator becomes extremely tired and consequently stable inspection results cannot be obtained, so inspection is duplicated by two or three people. Therefore, a scratch inspecting device based on image processing has been sought.

A conventional scratch inspection device based on image processing is disclosed in Japanese Unexamined Patent 7-103905, for example.

As shown in FIG. 22, in this device, light is shined onto an object under inspection 60, such as a crystal blank, from three directions by providing illumination sources 61~63 in positions mutually separated by 90°, and CCD cameras 64, 65 are placed between the illumination sources. These CCD cameras 64, 65 and the illumination sources 61~63 are placed in positions having an angle of 45° with respect to the horizontal face of the object under inspection. To inspect scratches, one of the cameras and one of the two illumination sources on either side of this camera are turned on at the same time, and the other illumination sources and cameras are turned off. Four images are taken by the cameras 64, 65 by implementing the four on and off combinations, thereby covering a 360° detection range. Each image is recorded in image input means 66, and judgement processing is implemented for each of these image signals, respectively, by feature extracting means 67 and quality judging means 68, to detect flaws, such as scratches which are independent of the direction of fracture, and the like.

However, the following problems are associated with the conventional technology described above.

1. Since the illumination and image-capturing operations are implemented obliquely using a plurality of illumination sources and cameras, equal quality in terms of focussing and light conditions setting cannot be ensured for all images, so accurate detection can be made.
2. Since the cameras are set in an oblique direction, the image becomes elliptical, so accurate dimensions and measurements cannot be obtained. In order to determine accurate dimensions and measurements, complex correctional processing is necessary.
3. Complex control is required for switching the cameras and illumination sources. Furthermore, in order to inspect one object, it is necessary to take a plurality of images, so the detection algorithm is complex and the image processing speed cannot be raised.
4. Since the cameras and illumination sources are both positioned at an angle of 45° with respect to the horizontal face, there is the risk that the background pattern of the mounting platform on which the object under inspection is mounted will be input. If the background pattern of the mounting platform is input, the SN ratio with respect to images of scratches or defects will deteriorate, thus making detection more difficult.

Therefore, in order to resolve the aforementioned problems, a scratch inspection device, whereby scattered light is shined onto the face of the object under inspection, such as a crystal blank, within an illumination angle of ±30°, from all sides of the perimeter of the object, has been investigated (Japanese Unexamined Patent 9-288063). By this means, since a dark field of view is illuminated from all sides of the perimeter of the object under inspection, and furthermore, since the illumination light is scattered light, reflected light reflected by scratches or edges is emphasized, and scratches or edges only stand out clearly in the image. Since there is no illumination at an angle greater than 30° with respect to the front or rear surface of the object under inspection, light which simply passes through the object under inspection and is reflected at the surface thereof does not form an image and therefore the image of the object under inspection as a whole forms a shadow and is not captured. The light forming an image is only the reflected light which is reflected either by scratches present in the object under inspection or the sides (edges) of the object under inspection. By image processing of this reflected light, scratches can be identified readily.

On the other hand, bevelling (chamfering) the outline (perimeter) of the crystal blank is used as a method for improving the characteristics of a crystal oscillator. In general, a cylindrical barrel system capable of high-capacity processing is used for bevelling. As illustrated in FIG. 23, this involves introducing a grinding material 42 into a cylindrical barrel 41 along with a plurality of crystal blanks 1 and grinding by causing the cylindrical barrel 41 to rotate. In order to improve crystal oscillator characteristics with good reproducibility, it is necessary to increase the accuracy of bevelling dimensions by means of the aforementioned method to achieve lateral and vertical symmetry.

In the aforementioned cylindrical barrel system, the bevelling state varies depending on the number of crystal substrates introduced into the barrel, the type of grinding material, the speed of revolution, and the like, and even if these conditions are kept uniform, this does not necessarily mean that the same bevelling state will always be achieved. Crystal substrate manufacturers rely on their own know-how to a large degree, but since this know-how is a variable factor, it cannot be regarded as an ideal approach, and currently uniform accuracy in bevelling dimensions cannot be maintained at all times and unexpected factors also arise. In order to improve accuracy in bevelling dimensions, a bevelling inspection method is required, which is capable of evaluating the state of bevelling of the crystal substrate surfaces, and feeding these results back to the bevelling process.

Since the bevelling process is achieved by applying extremely small scratches, a standard light field illumination method will not produce any significant difference between bevelled and unbevelled sections, so the bevelling state of the crystal substrate surfaces cannot be inspected by means of visual inspection by an operator, or by an image processing technique. Therefore, conventional inspection of bevelling has relied unavoidably on physical methods, such as (1) bevel measurement or (2) projection.

(1) Bevel measurement method

This method uses a laser height measuring device, and involves vapour deposition of reflective silver film onto the rear face of the crystal blank, whereupon a laser light source is shined onto the surface of the crystal blank and swept (scanned) in a diametrical direction (linear direction), and the level on straight lines is measured from the reflected light. By this means, the height of the surface in a linear direction of the crystal blank can be measured in a continuous fashion, and the state of bevelling can be determined from this surface height.

(2) Projection method

In this method, carbon powder (black) is coated onto the surface of a crystal blank, semi-transparent film or thin paper is pressed thereonto, and the carbon powder is transferred to the film or thin paper. The film bearing the transferred carbon is then projected in an enlarged state onto a screen. Since no carbon adheres to the unbevelled regions, the sate of bevelling can be observed visually from the state of transfer of the carbon powder.

On the other hand, if scratches in crystal blanks are inspected by image processing, the image signals read in are digitized in order to emphasize scratches, but it is necessary to set a threshold value for this digitization operation. The threshold value is an important parameter in determining the quality criteria applied to the inspection results. Conventionally, this threshold value is set as a uniform value for a crystal blank, regardless of the position on the blank.

Since a crystal blank cannot be used if it is scratched, a total product inspection is required rather than a sampling inspection. In view of the dramatic increase in demand for crystal blanks in recent years, it has become essential to achieve automation and increased speed in the aforementioned scratch inspection devices currently under investigation. In this case, a bottle-neck is caused by the mounting and dismounting of crystal blanks on the substrate mounting platform. Specifically, since the crystal blanks and substrate mounting platform both have mirror finishes, during mounting an air layer of almost uniform thickness is formed between the crystal blank and the substrate mounting platform, making the crystal blank liable to slip over the substrate mounting surface or causing the crystal blank to adhere to the substrate mounting surface once the air layer has been expelled after mounting. This phenomenon is particularly marked in cases where the substrate under measurement is 30 $\mu$m~500 $\mu$m thick, or in crystal blanks with edges or diameter between 3 mm~50 mm long.

Therefore, when a crystal blank conveyed by a conveyor robot arm of an automated device is mounted in the substrate mounting surface, the crystal blank may slide over the mounting platform, and the mounting position will be unstable, thus impeding accurate measurement. Moreover, after mounting, the crystal blank may be bonded tightly to the substrate mounting surface, preventing smooth a pick-up operation by the conveyor robot arm after inspection, and thereby obstructing the achievement of increased speed and automation in the inspection process.

Therefore, an operation whereby scratching is applied to the polished glass form of the mounting surface of the substrate mounting surface by applying sand thereto, such that the crystal blank does not slide or adhere tightly, has been investigated. However, if scratches are simply applied to the mounting surface to form small indentations, then slightly sharpened projecting sections will form at random on the mounting surface, which may break readily upon contact with a crystal blank, and even if quartz glass of similar hardness to the crystal is used for the mounting platform, then within several hours the tips of these projecting sections will wear away and will become difficult to distinguish from scratches on the crystal blanks, thereby impeding detection of scratches. Moreover, dirt may enter into the small indentations and this dirt is not readily removed, even by wiping, and if it adheres to the crystal blank, then it may be difficult to distinguish from scratches.

On the other hand, there have been the following problems with the conventional bevelling inspection methods described above.

(1) Level measurement method

Although the height of the polished surface can be measured accurately, since data is only obtained for the straight lines in which the crystal blank is scanned, it is not possible to inspect bevelling with respect to the whole surface of the crystal blank. If the scan in the horizontal direction is shifted in the vertical direction, surface data will still be obtained, but data omissions corresponding to the pitch width in the vertical direction will inevitably occur. Therefore, it is difficult to inspect the whole surface of a crystal blank. Moreover, since a process for vapour deposition of silver onto the rear surface is required, the inspection becomes a sampling process, which takes up time, and furthermore, the inspected samples cannot be used.

(2) Projection method

Although the whole surface of the crystal blank can be inspected, since it is necessary to take a sample crystal blank, and perform the transfer and projection operations, the inspection becomes a sampling process, which takes a very large amount of time. Since the method is based on visual observation, inspection data is not obtained.

In this way, neither of the methods (1) or (2) above allow inspection in real time, and both take up a large amount of time. Furthermore, since an integrated inspection method cannot be established, standardization with bevelling inspection cannot be achieved either. Moreover, since suitable data cannot be obtained, a feedback operation, which is effective in bevelling process technology, cannot be implemented.

Furthermore, since a batch method handling large quantities is used for the bevelling process, there are differences in the bevelling state between crystal blanks, and variations are also produced in subsequent etching processes using acid treatment. Regardless of this, as no inspection standards are set, it is difficult to determine tolerances and satisfactory items may be treated as defective, whilst defective items may be treated as satisfactory.

On the other hand, in conventional scratch inspecting methods, scratches are inspected by applying uniform inspection standards across a whole crystal blank, irrespective of the point of scratch inspection. However, crystal blanks forming the object under inspection usually incorporate some variation acquired during the manufacturing stages and they cannot be produced in a completely uniform manner, in addition to which, in some cases, more lenient standards can be applied depending on the region within the crystal blank. Therefore, if scratches are inspected according to a single inspection standard, instances where a satisfactory item is judged to be defective or where a defective item is judged to be satisfactory may occur. Furthermore, even if scratch inspection data based on image processing is obtained, since information relating to the inspection point is not entered, it is effectively impossible to acquire data for standardization of inspection or analysis control. This problem is not limited to scratches, but also arises in relation to inspection of the state of bevelling (chamfering).

SUMMARY OF THE INVENTION

It is an object of the present invention to overcome the aforementioned problems of the prior art, by providing a crystal substrate mounting platform and crystal substrate scratch inspection device, whereby handling of crystal substrates with respect to the mounting platform can be simplified.

It is a further object of the present invention to overcome the problems of the prior art by providing a bevelling inspection method and device for crystal substrates, whereby the bevelling state can be inspected visually in real time by image processing.

It is yet a further object of the present invention to overcome the problems of the prior art by providing an inspection method for crystal substrates, whereby scratches and the bevelling state in crystal substrates can be determined effectively.

The transparent substrate mounting platform according to the present invention is a mounting platform for mounting transparent substrates, in a substrate processing section for carrying out prescribed processes with respect to transparent substrates conveyed in and out by a conveying mechanism, wherein the mounting platform is made from a transparent material and indentations, such as grooves, holes, or the like, are formed in a flat mounting surface on which the transparent substrates are mounted. The transparent substrates may be a crystal substrates, sapphire substrates, SAW devices, diamond substrates, or ceramic substrates.

A transparent substrate is conveyed to a substrate processing section for carrying out processing, such as optical inspection, or the like, by a conveying mechanism, and it is mounted on a mounting platform in the substrate processing section. Here, since indentations, such as grooves, holes, or the like, are provided in the flat mounting surface of the mounting platform, there is no formation of an air layer of uniform thickness over the whole lower face of the transparent substrate, which might cause the substrate to slide, and therefore the transparent substrate can be placed in a desired position on the mounting surface, without sliding. Furthermore, since an air layer is preserved between the transparent substrate and the indentations in the mounting platform after mounting, the transparent substrate does not adhere (stick) tightly to the mounting platform and when the transparent substrate is picked up by the conveying mechanism, or the like, it can be detached readily from the mounting platform. Furthermore, since the transparent substrate is supported by a flat mounting surface, the occurrence of scratching due to contact between the mounting surface and the transparent substrate can also be reduced.

The indentations in the mounting surface should be fabricated by forming grooves, holes, depressions, or the like, by grinding or etching, in the mounting surface which is ground flat to a mirror surface, or the like. The size, layout and depth of the indentations with respect to the mounting surface is set in accordance with the dimensions, etc. or the transparent substrate, within a range wherein no sliding or adhesion of the transparent substrate is produced. In addition to crystal blanks for crystal oscillators and filters, the transparent substrates also include crystal lenses, or the like, for video cameras and DVDs.

In the foregoing invention, sapphire is used as the transparent material for the mounting surface, and since sapphire is harder than crystal, it is not scratched by the transparent substrate and it can be used for stable inspection, or the like, for a long period of time. Furthermore, the boundary regions between the flat mounting surface of the aforementioned mounting platform and the indentations should be formed such that they meet in a smooth curve. If the boundary regions (edge regions) between the mounting surface and the indentations have sharp edges, then during optical measurement, or the like, reflection will occur at the edge regions, and the transparent substrate may be scratched.

Furthermore, the scratch inspection device for transparent substrates according to the present invention is a scratch inspection device, whereby scratches are detected on the basis of an image signal of a transparent substrate captured by shining light onto the transparent substrate, comprising: a mounting platform made from a transparent material, wherein indentations, such as grooves, holes, or the like, are formed in a flat mounting surface on which a transparent substrate is mounted horizontally; illumination means for shining scattered light, diffused within an illumination angle of ±30° in a vertical direction with respect to the horizontal substrate face of the transparent substrate, from all sides of the perimeter of the transparent substrate; and image capturing means for capturing an image of a transparent substrate from a vertical direction with respect to the substrate face of the transparent substrate.

In this invention, scattered light, diffused within an illumination angle of ±30° in a vertical direction with respect to the horizontal substrate face of the transparent substrate, is shined from all sides of the perimeter of the transparent substrate by the illuminating means to create a dark field of view with respect to the image capturing means for capturing an image of a transparent substrate from a vertical direction with respect to the substrate face of the transparent substrate. Therefore, light which passes straight through the transparent substrate or is reflected by the substrate face, does not reach the illumination means, so an overall image of the transparent substrate is not taken. The light reaching the image capturing means is only the reflected light or scattered light reflected by scratches present in the transparent substrate or by the sides (edges) of the transparent substrate. Since the light is shined from all sides of the perimeter of the transparent substrate and within an illumination angle range of ±30° in a vertical direction with respect to the substrate face, and furthermore, since this light is diffused light or scattered light, the light reflected by scratches or edges is emphasized, and scratches and edges only stand out clearly in the image. By processing this image, scratches can be detected readily. Furthermore, since this invention uses a mounting platform made from a transparent material wherein indentations, such as grooves, holes, or the like, are formed in a flat mounting surface whereon a transparent substrate is mounted horizontally, it is possible to prevent sliding or adhesion of the transparent substrates, and the transparent substrates can be handled simply and quickly.

In the scratch inspection device according to the present invention, if the illumination means is provided below the transparent substrate, it will cause an obstruction when moving the transparent substrates, and smooth inspection can be carried out. Furthermore, desirably, light-emitting diodes are used as the aforementioned illumination means. Light-emitting diodes have markedly lifespan than conventional illumination sources, such as halogen lamps, or the like, and they produce less heat and are easier to handle. Light-emitting diodes producing concentrated light or diffused light may be used. If there are irregularities in the light shined on the transparent substrate, stable measurement cannot be achieved, but by providing a plurality of reflecting plates, such as mirrors, surrounding the diodes, light can be shined uniformly onto the transparent substrate, and diffusing plates do not need to be used in conjunction with the light source.

On the other hand, the bevelling inspection method for transparent substrates according to the present invention comprises the steps of: shining scattered light, diffused within an illumination angle of ±30° in a vertical direction with respect to the horizontal substrate face of a transparent substrate, from all sides of the perimeter of the transparent substrate; capturing an image of the transparent substrate from a perpendicular direction to the substrate surface of the illuminated transparent substrate; and reading in the captured image of the substrate surface of the transparent substrate, and carrying out a bevelling inspection from the image read in.

If a transparent substrate is subjected to a bevelling process according to an existing method, countless small scratches invisible to the naked eye are made on the substrate surface, and the perimeter regions of the substrate where these scratches are concentrated form a bevelled region. If scattered light is shined within an illumination angle of ±30° with respect to the substrate face from all sides of the perimeter of a transparent substrate which has undergone this bevelling process, and an image is taken from directly above the substrate face, then since a dark field of view is created by shining light from all sides of the perimeter of the transparent substrate and since this light is scattered light, light reflected by small scratches or the outline (edges) of the transparent substrate are emphasized, and only the small scratches or edges of the transparent substrate stand out in the image, thereby making it possible to distinguish bevelled regions from unbevelled regions.

Since no light is shined from a greater angle than 30° with respect to the front or rear face of the transparent substrate, light which passes straight through the transparent substrate or is reflected at the surface thereof, is not captured on the image, and therefore the unbevelled regions of the transparent substrate lie in shadow. According to existing methods, since transparent substrates are inserted whole into a cylindrical barrel and their perimeter regions are bevelled, a number of scratches are also formed unavoidably on the unbevelled region in the centre of the substrate. Therefore, the unbevelled region does not form a complete shadow, but forms a slight image. Consequently, the light captured on the image comprises clear reflected light reflected by the edges, and reflected light from the bevelled and unbevelled regions, inside the edges, which has a visibly discernible difference in intensity. The bevelled region of the transparent substrate surface can be seen and identified from this reflected light.

The present invention is also a bevelling inspection method for transparent substrates wherein, in the foregoing, a bevelling inspection is carried out by digitizing the image read in.

Digitized data is obtained for the whole transparent substrate surface by image processing and digitizing the reflected light. The threshold value used here is set automatically for each substrate. If the digitized data is converted to an image, the unbevelled and bevelled regions stand out clearly in the image by means of a two-step dark/light gradation. Therefore, the bevelling state can be seen readily from the digitized image.

Furthermore, the present invention is a bevelling inspection method for transparent substrates wherein, in the foregoing, the digitized data is subjected to statistical processing, and a bevelling inspection is carried out on the basis of the results of this processing.

The digitized data obtained is subjected to statistical processing by means of a commonly known method. The bevelling state over the whole surface of the substrate can be seen objectively from the results of this statistical processing.

The present invention is also a bevelling inspection device for transparent substrates, whereby a bevelling inspection is carried out on the basis of an image signal of a transparent substrate captured by shining light onto a transparent substrate which has undergone bevelling, comprising: a mounting platform made from a transparent material, wherein indentations, such as grooves, holes, or the like, are formed in a flat mounting surface on which a transparent substrate is mounted horizontally; illumination means for shining scattered light, diffused within an illumination angle of ±30° in a vertical direction with respect to the horizontal substrate face of a transparent substrate, from all sides of the perimeter of the transparent substrate; and image capturing means for capturing an image of the transparent substrate from a perpendicular direction to the substrate surface of the transparent substrate.

Furthermore, the present invention is a bevelling inspection device for transparent substrates, comprising: a substrate supplying device for supplying transparent substrates; a conveyor robot for conveying transparent substrates supplied by the substrate supplying device to a mounting platform; a mounting platform made from a transparent material, wherein indentations, such as grooves, holes, or the like, are formed in a flat mounting surface on which a transparent substrate conveyed by the conveyor robot is mounted horizontally; illumination means for shining scattered light, diffused within an illumination angle of ±30° in a vertical direction with respect to the horizontal substrate face of a transparent substrate mounted on the mounting platform, from all sides of the perimeter of the transparent substrate; image capturing means for capturing an image of the transparent substrate from a perpendicular direction to the substrate surface of the transparent substrate illuminated by the illumination means; and an image processing device for extracting scratches caused by bevelling present on the transparent substrate, from an image signal captured by the image capturing means, and carrying out statistical processing on the basis of the extracted signal.

A transparent substrate supplied by the substrate supplying device is conveyed to the mounting platform by the conveyor robot. The transparent substrate conveyed to the mounting platform is surrounded by light from a low angle by the illumination means. Small scratches in the transparent substrate caused by bevelling are made to stand out by this illumination, and the bevelled and unbevelled regions can be distinguished in the image. This image is captured by the image capturing means, and input to the image processing device, where it is digitized to emphasize the differences therein, such that the bevelled and unbevelled regions can be distinguished clearly from each other. The digitized data is subjected to statistical analysis and supplied for bevelling inspection. The conveying means conveys the transparent substrate whose image has been captured to the subsequent state, and it conveys a new transparent substrate supplied by the substrate supplying device to the mounting platform. Thereby, instead of conventional bevelling analysis, which has conveys a rather haphazard impression, it is possible to provide strong, path-breaking tools for mass analysis, thereby enabling analysis and control relating to whether or not the bevelling state is over specification to be carried out statistically.

The present invention is also a bevelling inspection device for transparent substrates wherein, in the foregoing invention, the illumination means are provided below the transparent substrate.

The present invention is also a bevelling inspection device for transparent substrates wherein, in the foregoing invention, light-emitting diodes are used as the illumination means.

In the foregoing invention, preferably, sapphire is used as the transparent material for the transparent substrate mounting platform.

Furthermore, in the foregoing invention, preferably, the boundary regions between the flat mounting surface and the indentations in the mounting platform are formed such that they are smoothly connected.

On the other hand, the present invention is an inspection method for transparent substrates comprising the steps of: dividing an image of the substrate surface of a transparent substrate into a plurality of regions when inspecting a transparent substrate; setting inspection standards required for the regions individually for each of the regions; and inspecting each region in accordance with the set inspection standards.

Usually, in transparent substrates, different inspection accuracy is required in different regions of the substrate, but in a conventional method, the whole substrate is treated as one item, and therefore the same inspection standards are applied. With regard to this point, in the present invention, since an image of the substrate surface of a transparent substrate is divided into a plurality of regions when inspecting a transparent substrate and inspection standards required for the regions are set individually for each of the regions, a single transparent substrate can be inspected according to different standards for each region of the substrate, depending upon requirements. Therefore, it is possible to distinguish accurately between satisfactory and defective items. Moreover, by subjecting the data obtained as a result of this inspection process to statistical processing, analysis can be made with respect to the individual regions, which is beneficial for evaluation purposes.

Preferably, in cases where the transparent substrates are thin strip-shaped substrates, the image of the substrate surface is divided into: corner regions at the four corners of the substrate; a pair of band-shaped upper and lower regions running parallel to the upper and lower edges of the substrate, minus the corner regions, and taking the upper or lower edge as one of their edges; a pair of band-shaped left and right-hand regions running parallel to the left and right-hand edges of the substrate, similarly minus the corners regions, and taking the left or right-hand edge as one of their edges; and a central region surrounded by the upper and lower regions and the left and right-hand regions. The inspection may involve scratch inspection, bevelling inspection or shape inspection.

BRIEF DESCRIPTION OF THE DRAWINGS

FIG. 1 shows one embodiment of a scratch inspection device for a crystal substrate relating to the present invention.

FIG. 2 shows the mounting platform in FIG. 1.

FIG. 3 is a theoretical illustration of a scratch appearing when light is shined from all sides of the perimeter of a crystal blank.

FIG. 4 shows a further embodiment of illumination means used in a scratch inspection device for crystal substrates according to the present invention.

FIG. 6 illustrates the shapes of boundary regions (edge regions) between the mounting surface of a mounting platform and indentations, according to changes in brush grinding time: FIG. 6(a) is a sectional view of a case where brush grinding is carried out for 0.5 H; and FIG. 6(b) is a sectional view of a case where brush grinding is carried out for 1.0 H.

FIG. 7 shows illumination images of a mounting platform and crystal blank corresponding to FIG. 6: FIG. 7(a) is an image of a case where a mounting platform which has been subjected to brush grinding for 0.5 H is used; and FIG. 7(b) is an image of a case where a mounting platform which has been subjected to brush grinding for 1.0 H is used;

FIG. 9 shows a further embodiment of the illumination means.

FIG. 13 shows an image of a bevelling state of a sample according to this embodiment: FIG. 13(a) is an image before digitization and FIG. 13(b) is a digitized image;

FIG. 14 shows an image of the bevelling state of a further sample according to this embodiment.

FIG. 15 is a characteristics curve plotting statistical processing data relating to FIG. 13(b);

FIG. 16 is a characteristics curve plotting statistical processing data relating to FIG. 14(b);

FIG. 21 is a diagram illustrating a personal computer setting screen for bevelling inspection according to an embodiment;

FIG. 22 is a general compositional diagram of a conventional scratch inspection device for transparent substrates.

DESCRIPTION OF THE PREFERRED EMBODIMENTS

Figure 1A:
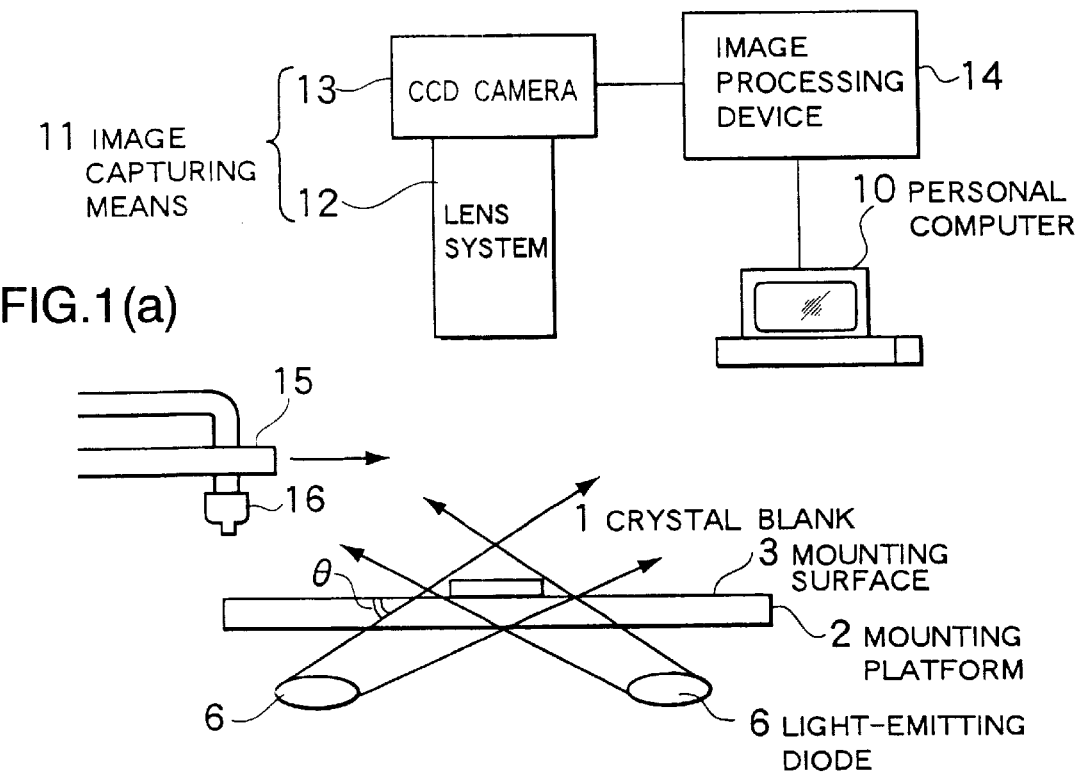
FIG. 1(a) is a general compositional view.
Figure 1B:
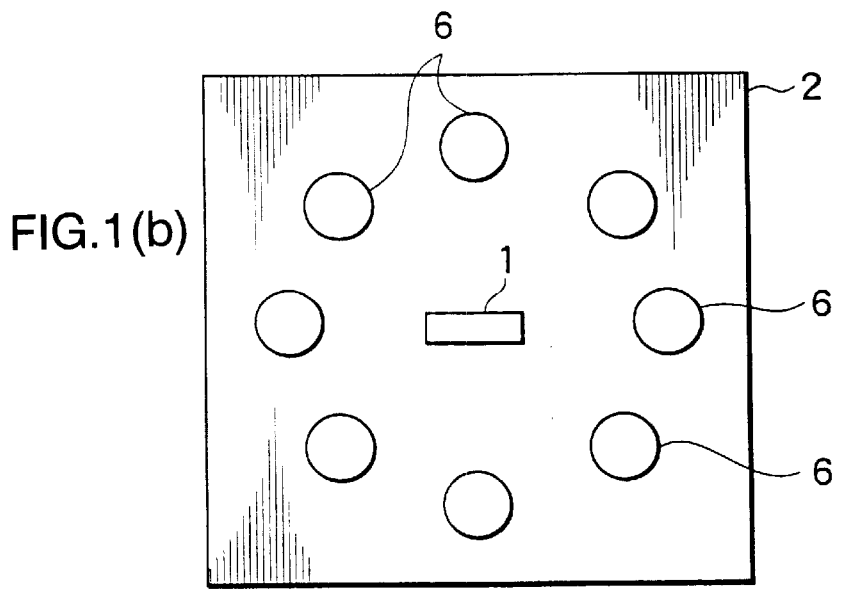
FIG. 1(b) is a under view of light-emitting diodes and a mounting platform.

Firstly, an embodiment of the crystal substrate mounting platform and crystal substrate scratch inspection device according to the present invention are described with reference to the drawings. FIG. 1 is a general compositional view showing one embodiment wherein a crystal substrate scratch inspection device according to the present invention is applied to a crystal blank for a crystal oscillator.

In FIG. 1, 1 is a short plate-shaped crystal blank having a mirror finish, which generally has a size of 1×3 mm~3×10 mm, and thickness of approximately 30 $\mu$m~500 $\mu$m. The crystal blank 1 has a short plate shape, but it is not limited to this and may also have a circular shape of 4~8 mm diameter.

Figure 2A:
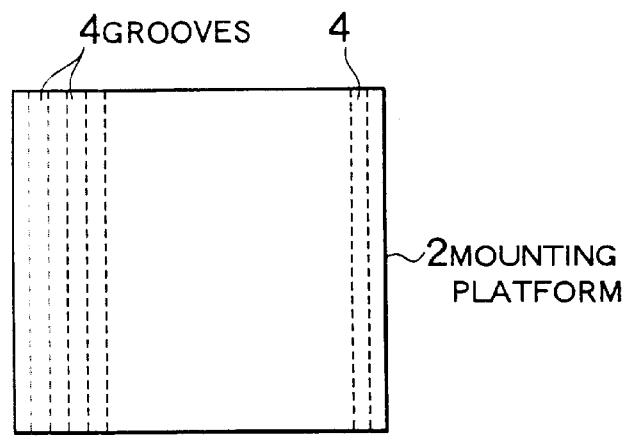
FIG. 2(a) is a plan view.
Figure 2B:
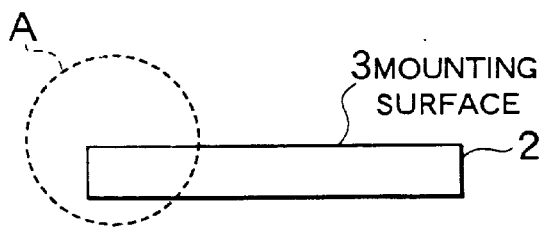
FIG. 2(b) is a side view.
Figure 2C:
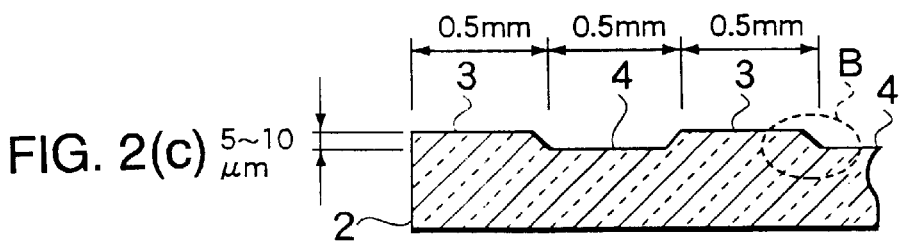
FIG. 2(c) is an enlarged view of section A in FIG. 2(b)
Figure 2D:
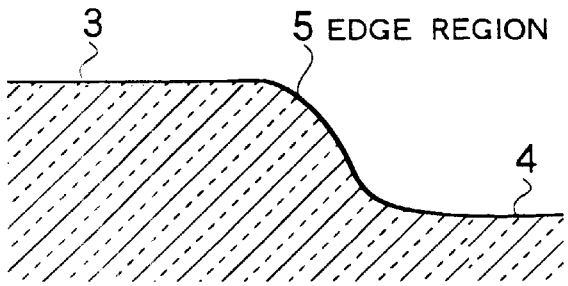
FIG. 2(d) is an enlarged view of section B in FIG. 2(c)

The crystal blank 1 is mounted horizontally on the mounting platform 2. The mounting platform 2 is made from sapphire and in order to prevent sliding or adhesion of the crystal blank 1, grooves 4 are formed as indentations in the mirror-finished mounting surface 3 of the mounting platform 2, as illustrated in FIG. 2. A plurality of grooves 4 are formed equidistantly in parallel to one edge of the mounting platform 2. Specifically, grooves 4 of 0.5 mm width and 5~10 $\mu$m depth are fabricated by grinding on the mounting platform 2, which is 20×20 mm in size and 1 mm thick, as illustrated in FIG. 1(c), which gives an enlarged sectional view of section A in FIG. 2(b). Moreover, the edge sections (border sections) between the mounting surface 3 and grooves 4 are formed with a smooth curve, as shown in FIG. 2(d), which gives an enlarged sectional view of section B in FIG. 2(c), such that there is no optical reflection when scanning for scratches.

Sapphire is used for the mounting platform 2 because it is harder than crystal and therefore will not be scratched by the crystal blank 1. However, since a composition is adopted wherein the crystal blank 1 is mounted on the mirror-finished mounting surface 3, the material for the mounting platform 2 is not limited to sapphire, and even if a normal glass, such as soda glass, crystal glass, or the like, is used, no scratching is liable to occur. It is also possible to use diamond or ceramic which is transparent to the inspection light for the mounting platform 2.

Since the grooves 4 in the mounting platform 2 are formed mutually parallel in one direction, if air etc. is blown in the direction of the grooves 4, dirt which has entered into the grooves can be removed readily. Moreover, in the aforementioned embodiment, the grooves 4 are formed mutually in parallel, but it is also possible to form the grooves such that they intersect, for instance, in a lattice shape. Alternatively, instead of grooves cylindrical or other shaped holes may be formed as indentations in the mounting surface in an appropriate configuration.

Light-emitting diodes 6 are provided on the under side of the crystal blank 1 such that they surround the crystal blank 1, as illustrated in FIG. 1. Light from the light-emitting diodes 6 is shined onto the substrate surface of the crystal blank 1 within an illumination angle (of 0°~-30° in the vertical direction, from all sides of the perimeter of the crystal blank 1 by means of the mounting platform 2. For the illumination angle), the front surface of the crystal blank 1 is taken as positive and the rear face thereof is taken as negative. If a mirror is positioned around the light-emitting diodes 6, then light can be shined uniformly onto the crystal blank 1 from all sides of the perimeter thereof. Moreover, the light-emitting diodes 6 should have high luminosity and emit light in the spectrum from red light to infrared light. The light-emitting diodes 6 forming the illumination means are positioned beneath the mounting platform 2 in order that there is no obstruction to the upper surface of the crystal blank 1 when it is moved, thereby making it compatible with automation and mass production application of the inspection process.

On the other hand, image capturing means 11 are provided directly above the surface of the crystal blank 1 such that the direction in which the image is taken is perpendicular thereto. The image capturing means 11 is set such that the field of view only covers the region of the crystal blank 1, using, for example, a lens system 12 which focuses light from the CCD camera 13 and crystal blank 1 onto the CCD surface of the CCD camera 13. By adopting this composition, light incident obliquely on the crystal blank 1 from the light-emitting diodes 6 does not enter directly into the lens system 12 and is therefore in a dark field state.

An image signal captured by the CCD camera 13 is input to a image processing device 14. This image processing device 14 comprises a feature extracting section for extracting scratch features present on the crystal blank 1 from the input image signal, and a judging section for judging whether scratches are present on the basis of the extracted signal. The image capturing means 11 has only the region of the crystal blank in its field of view, and therefore the image processing device 14 is capable of detecting scratches by processing brightness changes in the field of view at high speed.

The crystal blank 1 is sucked up by a vacuum chuck 16 and conveyed to the mounting platform 2 by means of a conveyor robot arm 15, and after scratch inspection, it is sucked up again by the vacuum chuck 16 and conveyed away by the conveyor robot arm 15.

In the foregoing composition, the crystal blank 1 sucked up by the vacuum chuck 16 and conveyed to the mounting platform 2 by the conveyor robot arm 15 is mounted onto a prescribed position on the mounting platform 2. Here, since a plurality of grooves 4 are formed in the mounting surface 3 of the mounting platform 2, the crystal blank 1 is placed accurately in the prescribed position, without sliding over the mounting platform 2, and therefore, precise scratch measurement can be carried out.

When diffused scattered light from the plurality of light-emitting diodes 6 provided under the mounting platform 2 is shined towards the crystal blank 1, the crystal blank 1 is surrounded by the scattered light on all sides of the perimeter thereof. In this case, light must not be shined from directly above or below the crystal blank 1. If light is shined from directly above or below, the image of the crystal blank 1 will be captured by the CCD camera 13 due to transmitted or reflected light. Moreover, the background pattern of the mounting platform 2 holding the crystal blank 1 will be projected distinctly, and will be difficult to distinguish from scratches (defects) present in the crystal blank 1.

Figure 3A:
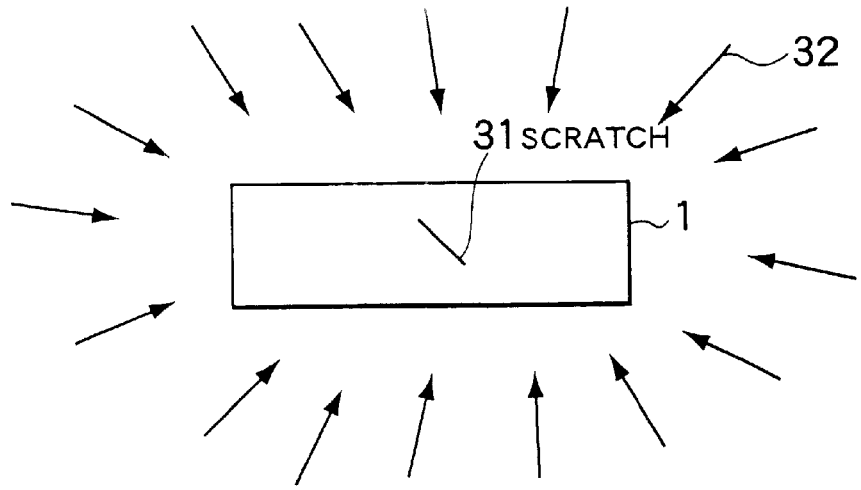
FIG. 3(a) is a plan view and FIG. 3(b) is a side view.
Figure 3B:
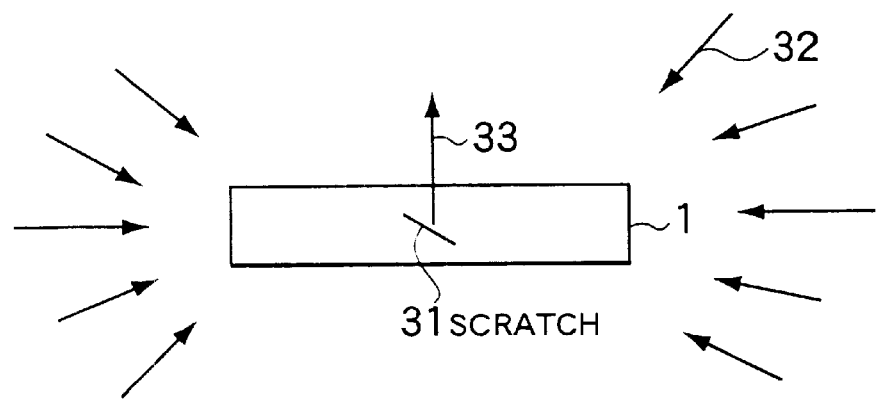

As shown in FIG. 3, if light is shined onto the crystal blank 1 from all sides of the perimeter thereof, the reflected light energy due to scratches (or defects) 31 or edge portions in the crystal blank 1 is large. Light is shined from all directions around the crystal blank 1 in the horizontal plane, due to scattering, but if there are no scratches in the crystal blank 1, then since the light path is not obstructed, the scattered light will be transmitted. However, if there are edges or scratches 31, then the light will hit these and become reflected light 33, thereby emphasizing their presence.

When the scattered light 32 hits a scratch 31, it is reflected and the scratch will be apparent on the surface of the crystal blank 1. Since light 32 is shined onto the scratch 31 from all directions, the energy of the light reflected by the scratch 31 is emphasized, and when the crystal blank 1 is observed from above, the scratch 31 appears distinctly. Since a scratch in crystal will have directional characteristics, if light is shined in one direction only, then scratches parallel to the light will not reflect the light and will therefore be difficult to detect, and furthermore, if light is shined in three directions, for example, then the SN ratio will be poor and scratches will be difficult to detect with high accuracy. However, by utilizing a light multiplying effect by directing light onto the scratch 31 from four or eight directions, or by concentrated application of diffused light, as in the present embodiment, it is possible to improve the SN ratio markedly, thereby enabling even small scratches to be detected accurately. In particular, scratches which are difficult to detect with the human eye (10~20 $\mu$m or less) can be detected by creating a relatively strong quantity of light.

Moreover, since an image of the whole of the crystal blank can be taken and processed as the field of view in one operation, even small scratches (10 $\mu$m or less) can be detected at high speed. For example, if processing as a 512 (512 image, scratches can be detected within 200 ms, and this time is the same no matter how scratches are present in a single crystal blank. Also, in the case of small scratches less than 10~20 $\mu$m in size, since the light energy is high and stable detection can be made, the process can be automated by image processing.

Furthermore, if the edge processing accuracy at the perimeter of the crystal blank is poor, then a large amount of light will be reflected at the edge portions, and conversely, if the accuracy is good, then a small amount of light will be reflected so the scratch inspection device according to the present embodiment can also be applied to investigating the processing accuracy of the crystal blank.

Preferably, the illumination angle of the light with respect to the upper surface of the crystal blank is +30°~−30°. This range is taken because within an illumination angle range of ±30° the SN ratio is high and the scratch 31 can be identified clearly, but if the angle lies outside this range, then the background pattern of the mounting platform will become more pronounced, making identification more difficult, and at an angle of ±45°, for example, the image of the scratch 31 will be absorbed completely by the background pattern, making the scratch 31 impossible to detect.

After scratch inspection, the crystal blank 1 is sucked up again by the vacuum chuck 16 and conveyed to the next stage by the conveyor robot arm 15. In this case, since grooves 4 are formed on the mounting surface 3 of the mounting platform 2, the crystal blank 1 is picked up smoothly in a stable conveyance operation, without adhering to, and refusing to separate from, the mounting platform 2.

In the present embodiment, as described above, since a plurality of grooves 4 are provided on the mounting surface 3 of the mounting platform 2, no air layer is created which may induce a sliding motion between the mounting platform 2 and the crystal blank 1, and therefore the crystal blank 1 does not slide over the mounting platform 2. Consequently, the crystal blank 1 can be set in a prescribed position on the mounting platform 2 simply by lowering the conveyor robot arm 15 and releasing the suction, thereby allowing accurate scratch inspection to be carried out. Moreover, the air layer is not completely expelled causing the crystal blank 1 to bond tightly to the mounting platform 2. Therefore, errors in the pick-up operation after inspection are avoided, and handling by vacuum pump can be conducted at high speed.

Figure 4A:
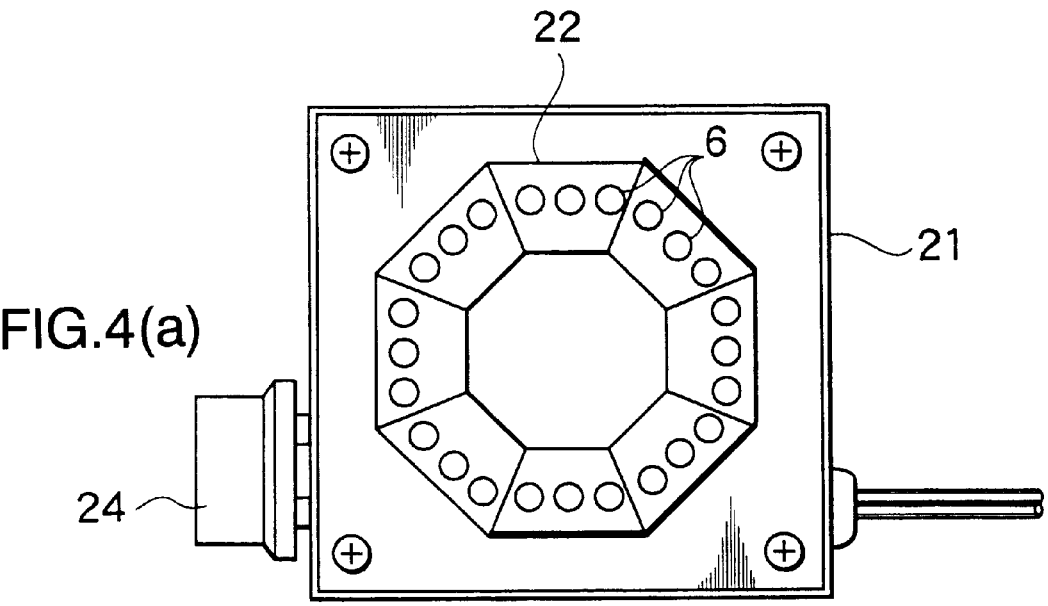
FIG. 4(a) is a plan view and FIG. 4(b) is a longitudinal section of a state where a crystal blank is mounted.
Figure 4B:
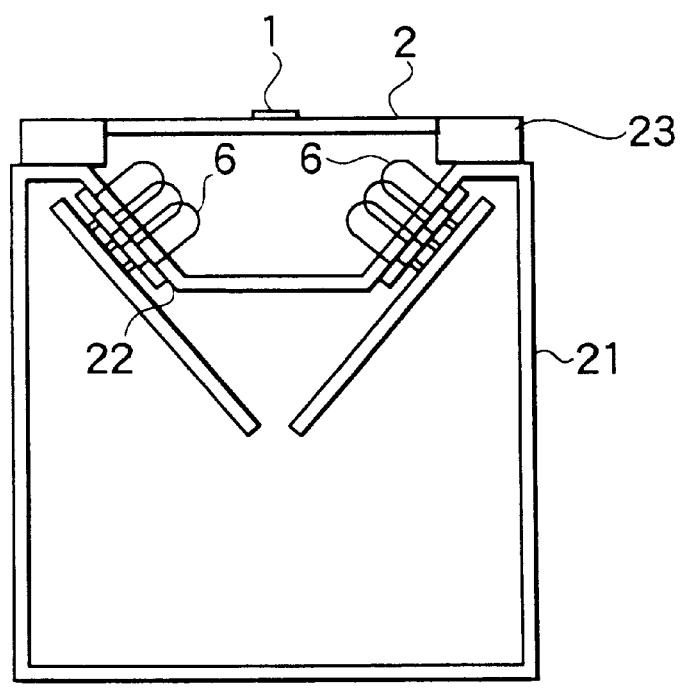

FIG. 4 shows a further embodiment of illumination means (light source) for shining light from below the crystal blank 1. The illumination means comprises an octagonal cone-shaped installation member 22, whereby light-emitting diodes 6 are installed on the upper portion of a box-shaped main unit 21, and a plurality of light-emitting diodes 6 provided around the oblique perimeter of the installation member 22. As illustrated in FIG. 4(b), the mounting platform 2 on which the crystal blank 1 is mounted is positioned on the main unit 21 by means of a seat 23, and light from the light-emitting diodes 6 is shined uniformly from below the crystal blank 1, from all sides of the perimeter thereof, by means of reflecting mirror, which is omitted from the drawings. In general, the transparency of the crystal blank is increased markedly by polishing. If the surface is made slightly rough by polishing using 2000~4000 grade polishing granules, the amount of light from the illumination means is reduced slightly such that scratches stand out more clearly, whilst if the surface is given a transparent finish using polishing granules of grade 4000 or above, then conversely, the light should be increased to emphasize the scratches. Therefore, the light output of the light-emitting diodes 6 is made adjustable by made of a light-adjusting knob 24.

Figure 5:
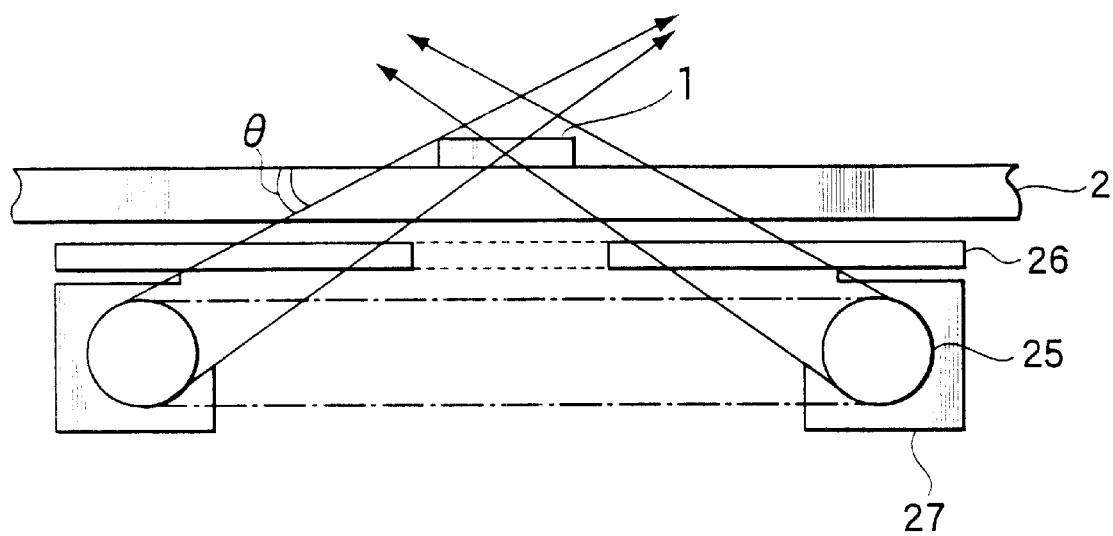
FIG. 5 is an approximate compositional view showing a further embodiment of illumination means used in a scratch inspection device for crystal substrates according to the present invention.

FIG. 5 shows yet a further embodiment of the illumination means. In this embodiment, a ring light 25 is used as a light source for shining light from all sides of the perimeter of a crystal blank 1, and this ring light 25 is positioned below the mounting platform 2. For the ring light, generally, a ring-shaped fluorescent lamp, which is simplest and most inexpensive, can be used. If a fluorescent lamp is used for the ring light 25, then since the light generated by the fluorescent lamp is already scattered light, it is not essential to provide a diffusing plate 26, but in order to increase the scattering effect, a ring-shaped diffusing plate 26, whereby light shined onto the crystal blank 1 from the ring lamp 25 is diffused such that scattered light is shined onto the crystal blank 1, should be provided in the direction of illumination of the ring lamp 25. A light-reducing filter, or the like, is used as the diffusing plate 26. Furthermore, in order to black out the portion of the ring light 25 which does not contribute to illumination, a light shield 27 is provided around the ring lamp 25, such that light can be shined from a sides of the perimeter of the crystal blank 1 within an illumination angle (of 0°~−30° with respect to the surface of the crystal blank 1.

As described previously, grooves are fabricated by grinding on the mounting surface of the mirror-polished mounting platform, and a smooth curve is given to the border regions between the mounting surface and grooves, such that there is no optical reflection during the scratch inspection process. Here, this point will be described in more concrete terms. In order to fabricate grooves in a mounting platform made from sapphire, brush grinding is carried out using a diamond grinding agent, followed by chemical polishing, and the occurrence or absence of optical reflection at the grooves is greatly reflected by the brush grinding time.

FIG. 6 shows cross-sections of boundary regions between the mounting surface and grooves in a sapphire mounting platform of 1 mm thickness in a concrete example; the horizontal axis indicates the lateral direction of the mounting platform, where the unit is 0.2 mm per 2 gradations, and the vertical axis indicates the groove depth, where the unit is 20 $\mu$m per 2 gradations. FIG. 6(a) shows a case where brush grinding was carried out for 0.5 hours (H) and the groove depth was 13 $\mu$m. FIG. 6(b) shows a case where brush grinding was carried out for 1.0 H, and the groove depth was 11 $\mu$m. Compared to FIG. 16(a), the boundary regions between the mounting surface and the grooves are more smoothly rounded, to an extent corresponding to the longer grinding time.

FIG. 7 shows an illuminated image of a mounting platform and crystal blank in a case where a mounting platform as shown in FIG. 6 was used. FIG. 7(a) is an image in a case where a mounting platform brush-ground for 0.5 H was used, and FIG. 7(b) is an image in a case where a mounting platform brush-ground for 1.0 H was used. As these illustrations demonstrate, when a mounting platform brush-ground for 0.5 H is used, optical reflection is produced by the grooves during scratch inspection, and the grooves stand out in the image are difficult to distinguish from scratches. However, when a mounting platform brush-ground for 1.0 H was used, this does not occur and there are no edging effects in the dark field due to grooves, so the light captured on the image in reflected light reflected by scratches present in the object under inspection or by the sides (edges) of the object under inspection. Therefore, the selection of the grinding time is important in producing optimal rounding at the boundary regions whilst maintaining the groove depth required to avoid sliding or adhesion.

Figure 8:
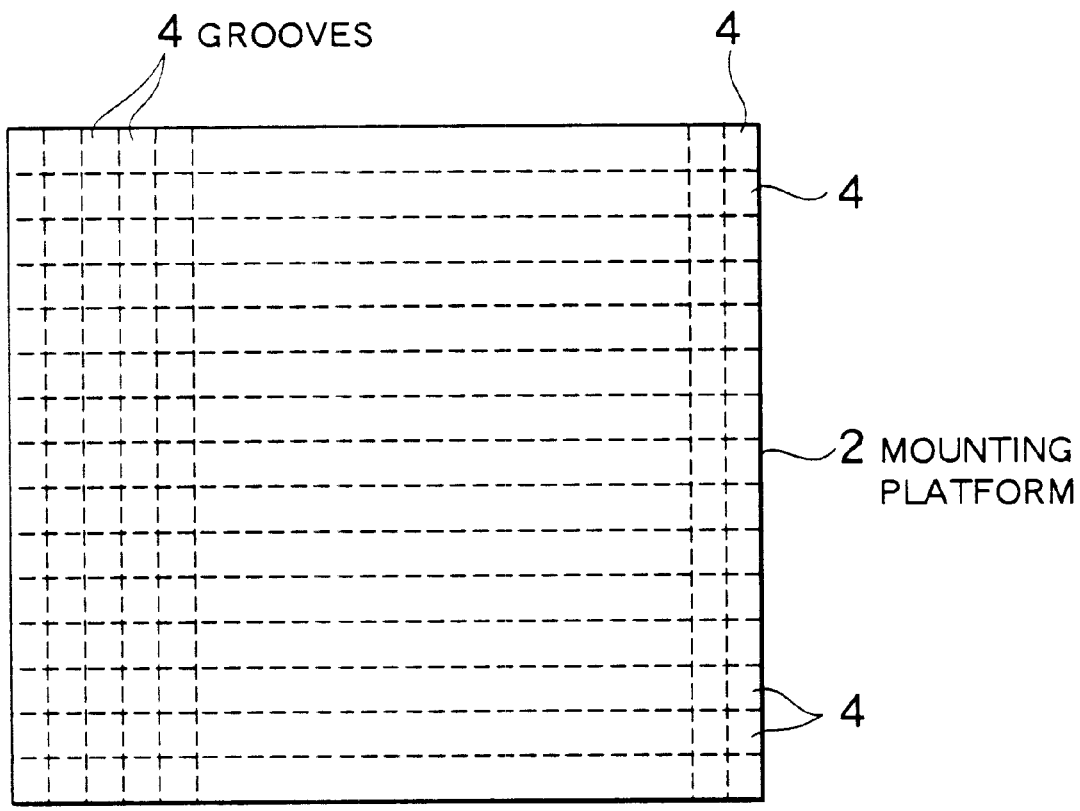
FIG. 8 is a plan view of a mounting platform illustrating a further embodiment wherein the grooves are mutually intersecting and form a lattice shape.
Figure 9A:
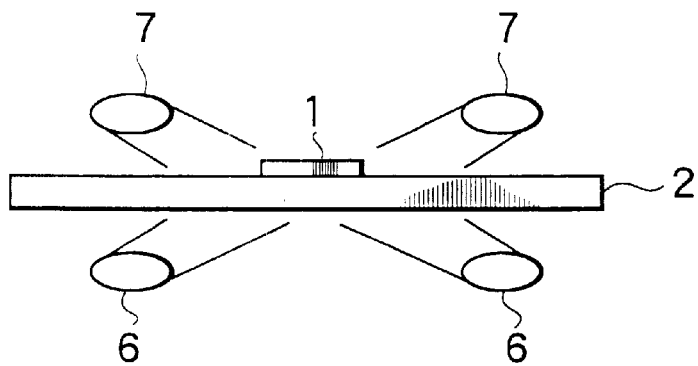
FIG. 9(a) is a general compositional view wherein illumination means are provided both above and below.
Figure 9B:
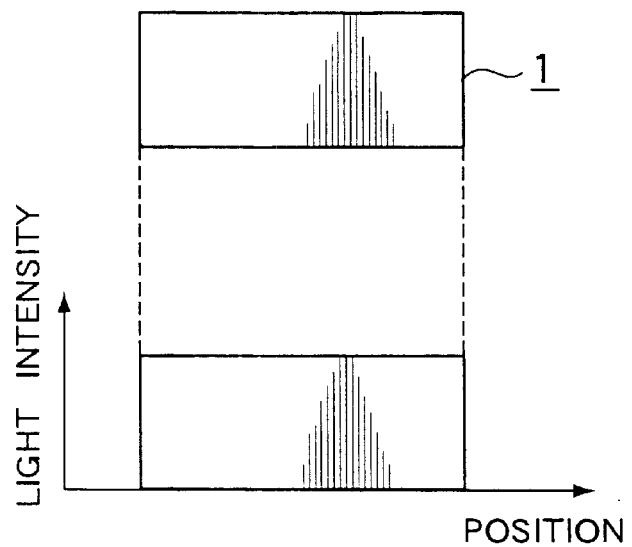
FIG. 9(b) illustrates the light intensity of a crystal blank when illuminated from above and below.
Figure 9C:
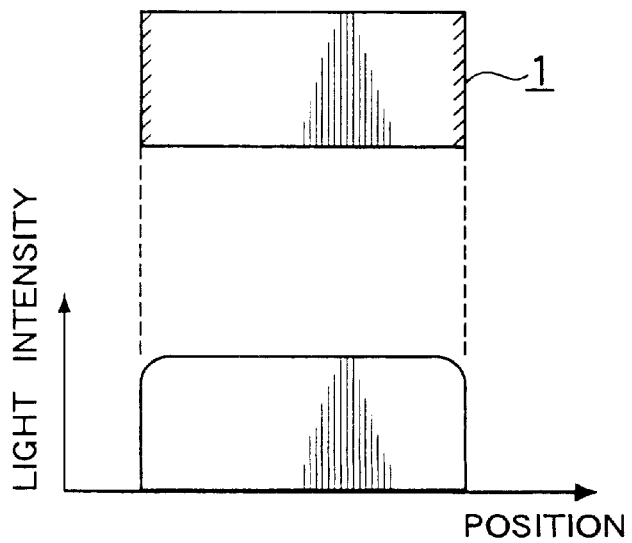
FIG. 9(c) shows the light intensity of a crystal blank when illuminated from below only.

FIG. 8 shows a further embodiment of a sapphire mounting platform, wherein the grooves 4 in the mounting platform 2 intersect with each other to form a lattice shape, as mentioned previously. If the grooves run mutually in parallel in one direction, as shown in FIG. 2, any dirt which has entered into the grooves can be removed simply, but with repeated use, dust and dirt will tend to accumulate on the peak sections between the grooves and after one or two days, this will become difficult to remove. This is thought to be due to the fact that the peak sections are formed in a linear shape and the surface area of the peak sections is high. Therefore, if the peak sections are formed into point shapes by fabricating the grooves 4 in a lattice configuration, the surface area of the peak sections is reduced. Accordingly, the accumulation of dust and dirt on the peak sections is reduced, and the maintenance cycle for the mounting platform can be extended FIG. 9 shows a further embodiment of the illumination means, whereby, in addition to light-emitting diodes 6 shining light onto the crystal blank 1 from below, supplementary light-emitting diodes 7 are also provided for shining light thereonto from above. In the case of a crystal blank 1 in shape of a thin strip, if the longer edges are over 8 mm long, the intensity of the light at either end region (shaded region) of the crystal blank 1 will be less than that in the central region thereof, so it will be difficult to detect edges. If the diameter of the configuration of light-emitting diodes 6 surrounding the crystal blank 1 is increased, the intensity of light at the end regions will be increased, but this requires improvements to existing equipment, and increases the size of the equipment. Therefore, by providing supplementary light-emitting diodes 7 above the object to illuminate the end regions (four corners) of the crystal blank, as shown in FIG. 9(a), the same quantity of light can be obtained in these regions as in the central region, as illustrated in FIG. 9(b). Provided that the intensity ratio of light from the upper and lower light-emitting diodes 6, 7 is in the range of 7:3~3:7, then there is no problem in terms of optical balance. Normally, it should be adjusted to 5:5. If light-emitting diodes 6 are provided on the upper side of the mounting platform 2, then they must be positioned such that they do not obstruct the conveyance path of the conveyor robot arm 15. Furthermore, illumination is provided within an illumination angle range of +30° with respect to the crystal blank surface.

Figure 10:
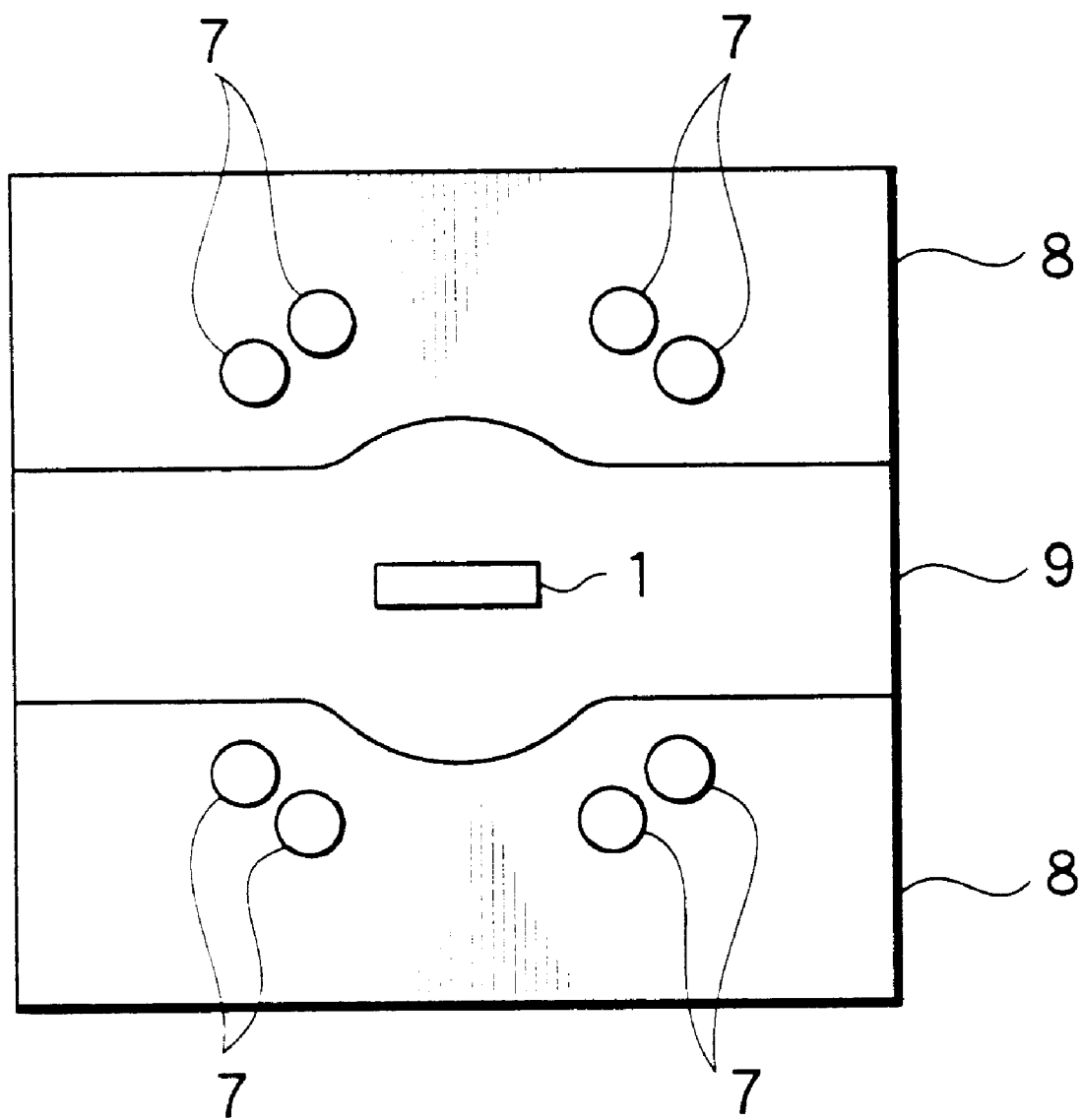
FIG. 10 is a plan view showing the configuration of supplementary illumination means.

FIG. 10 is a plan view showing a specific configuration of the supplementary light-emitting diodes 7. An installation plate 8 for installing the supplementary light-emitting diodes 7 has an opening in the centre region thereof, such that it does not cover all of the mounting platform, thereby ensuring the conveyance path 9 of the conveyor robot arm 15. The supplementary light-emitting diodes 7 are installed in four places on the installation plate 8 facing the four corners of the crystal blank 1, such that they can illuminate both end regions of the crystal blank 1 from above. In order to keep the illumination angle within +30°, the light path is restricted by mirrors, which are omitted from the drawings.

Figure 11:
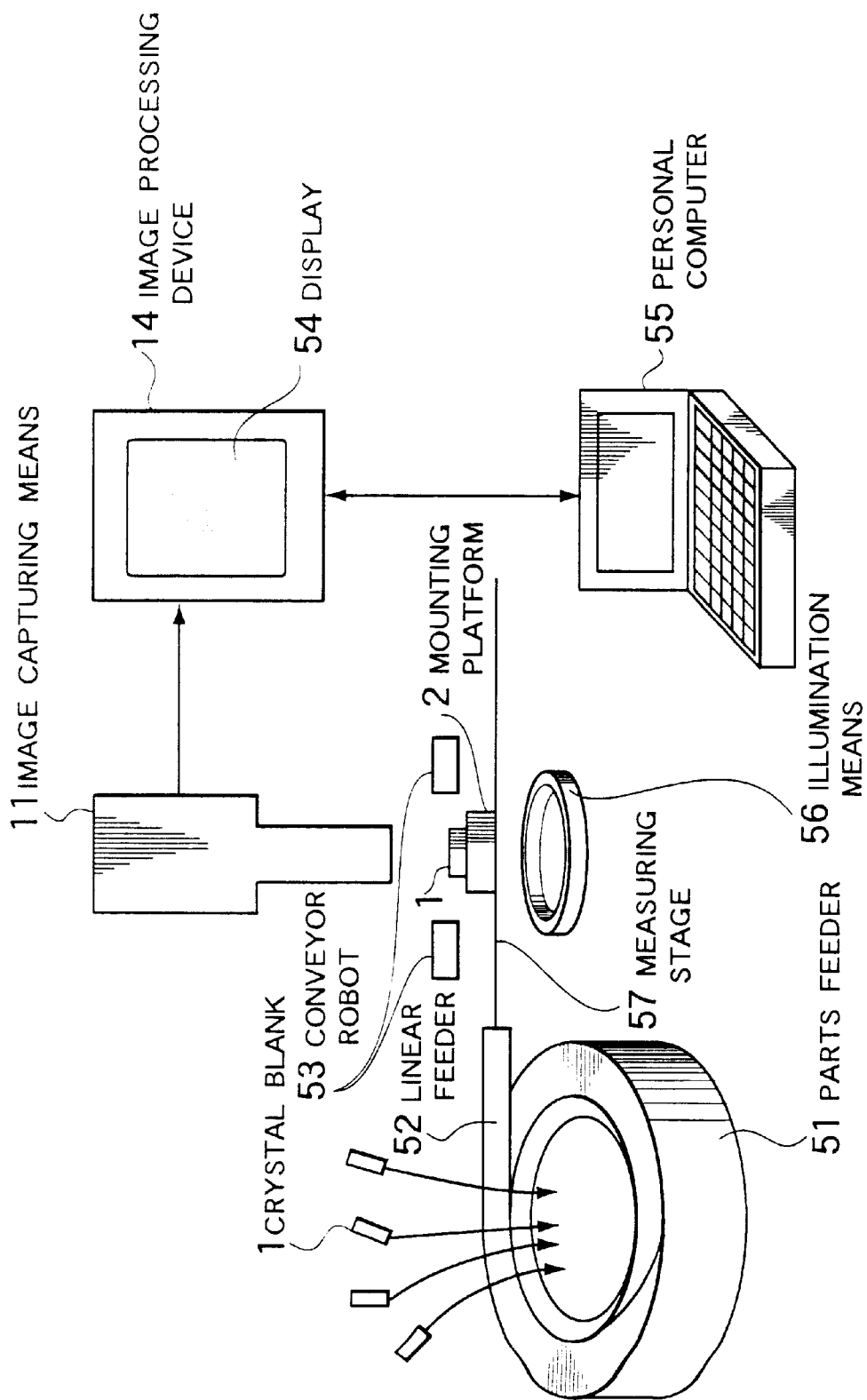
FIG. 11 is a general system diagram of an embodiment of a bevelling inspection device for crystal substrates relating to the present invention.

Next, an embodiment of a crystal substrate bevelling inspection method and device for same according to the present invention is described. FIG. 11 is a general compositional view showing one embodiment wherein the crystal substrate bevelling inspection device relating to the present invention is applied to a crystal blank for a crystal oscillator. The bevelling inspection device comprises the following elements.

A parts feeder 51, forming a substrate supplying device, accommodates a plurality of crystal blanks 1 in a random fashion and it is coupled to a linear feeder 52 whilst rotating, such that one or a plurality of units are supplied to an external measuring stage 57. A conveyor robot 53 comprises a suction arm and conveys one or a plurality of crystal blanks supplied to the measuring stage 57 by the linear feeder 52 to a mounting platform 2 provided on the measuring state 57. Furthermore, after inspection, the crystal blank 1 is retained on the mounting platform 2 and conveyed in the downstream direction of the measuring stage 57.

The mounting platform 2 is made from a sapphire substrate, or the like, and is composed from a transparent material wherein indentations, such as grooves, holes, or the like, for preventing suction of the crystal blank 1, are formed on a flat mounting surface whereon a crystal blank 1 conveyed by the conveyor robot 53 is positioned horizontally. The illumination means 56 comprises a fluorescent lamp, or the like, and it surrounds the crystal blank 1 with diffused scattered light from all sides of the perimeter thereof, within an angle of illumination range of ±30° in the vertical direction, with respect to the horizontal blank surface of the crystal blank 1 positioned on the mounting platform 2.

The image capturing means 11 comprises a CCD camera, or the like, which is set directly above the mounting platform 2 and takes an image of the crystal blank 1 from a perpendicular direction with respect to the blank surface of the crystal blank 1 illuminated by the illumination means 56. The image processing device 14 displays the image taken by the image capturing means 11 on a display 54, extracts scratches produced by bevelling present on the crystal blank 1 from the image signal, and conducts statistical processing on the basis of the extracted signal in order that the processed and non-processed regions of the crystal blank can be distinguished clearly from each other. The personal computer 55 inputs set values to the image processing device 14, and compiles the data obtained from the image processing device 14 using generic spreadsheet software to record the corresponding results.

The scratch inspection device for crystal substrates illustrated in FIG. 1 can be applied directly as the bevelling inspection device described above.

Figure 12:
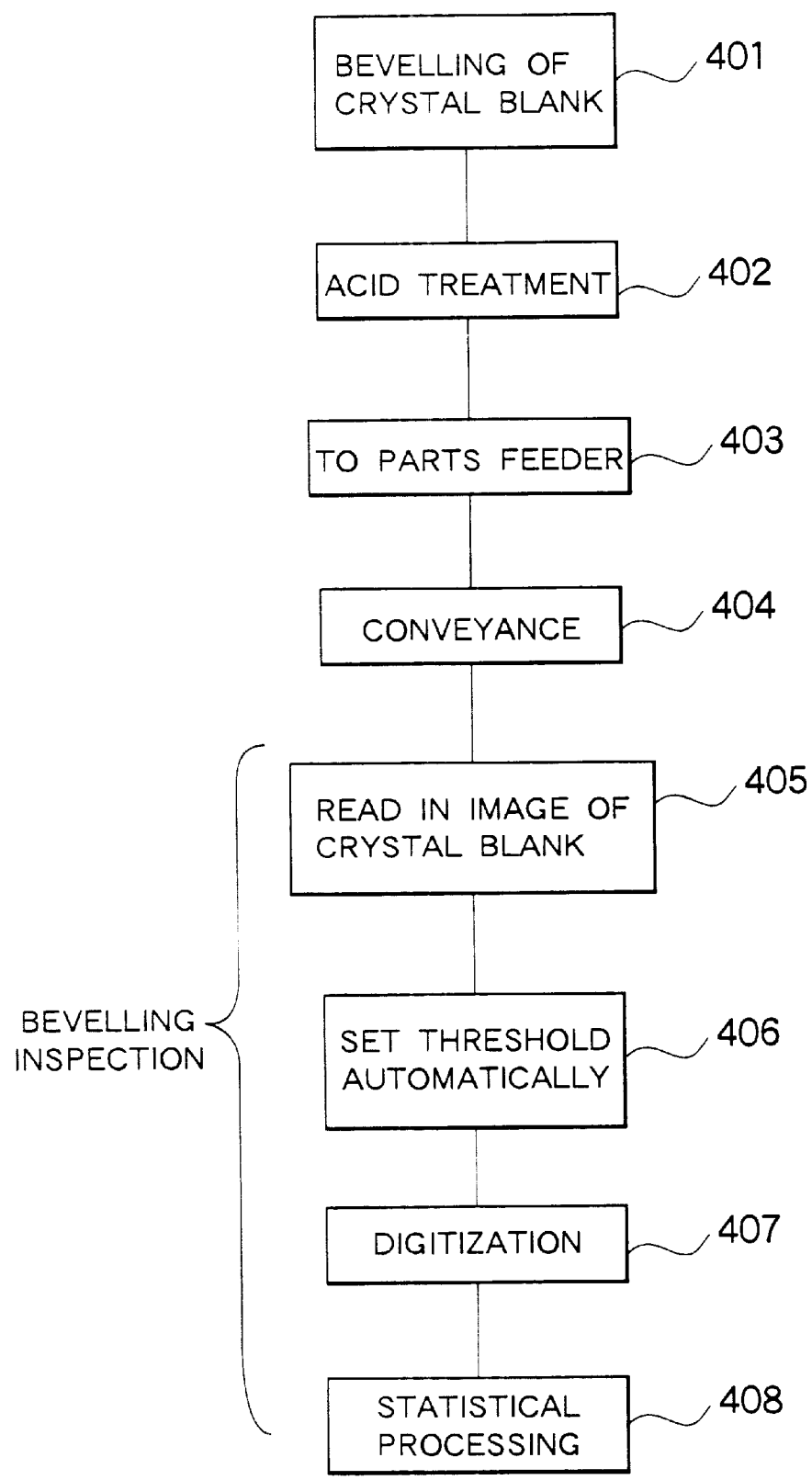
FIG. 12 is a flowchart of a sequence from bevelling up to bevelling inspection according to this embodiment.

In order to carry out bevelling inspection by means of the foregoing composition, the steps illustrated in FIG. 12 are followed. Firstly, crystal blanks undergo a bevelling process by means of a cylindrical barrel method (step 401). After this process, acid treatment using fluoric acid or the like, is carried out to make the surfaces smooth (step 402). This acid treatment is carried out in large batches, similarly to bevelling, so there is a dynamic variation within crystal blanks and between crystal blanks. Therefore, the threshold settings used for the subsequent digitization process are different for each crystal blank and need to be changed in response to variations, within allowable tolerances. After acid treatment, the crystal blanks 1 are introduced into the parts feeder 51 in lot units, and they are then supplied by the linear feeder 52 coupled to the measuring stage 57 (step 403). The supplied crystal blank 1 is sucked up by a vacuum chuck 16 and conveyed to the mounting platform 2 by the conveyor robot arm 15 (step 404). Thereupon, bevelling inspection is carried out (steps 405 * 408).

A crystal blank 1 conveyed to the mounting platform 2 is placed in a prescribed position on the mounting platform 2. Since a plurality of grooves 4 are formed in the mounting surface 3 of the mounting platform 3, during this operation, the crystal blank 1 is positioned accurately in the desired position, without sliding over the mounting platform 2, and therefore accurate inspection of scratches created by bevelling can be carried out.

If diffused scattered light is shined towards the crystal blank 1 from the plurality of light-emitting diodes 6 provided below the mounting platform 2, then the crystal blank 1 becomes surrounded by the scattered light on all sides of the perimeter thereof. In this case, light must not be shined from directly above or directly below the crystal blank 1. This is because if light is shined from directly above or directly below, the image of the crystal blank 1 will be captured by the CCD camera 13. Moreover, the background pattern of the mounting platform supporting the crystal blank 1 will be captured clearly, making it difficult to distinguish bevelling scratches present on the crystal blank 1.

Here, the judgement principles for small scratches formed during bevel processing are the same as those for larger scratches (or defects) as described in relation to FIG. 3.

Bevelling involves placing a crystal blank in a cylindrical barrel and grinding the perimeter of the blank by applying countless small scratches less than 10~20 μm in size. Therefore, if a crystal blank 1 which has had countless small scratches applied thereto by bevelling is illuminated at a low angle, as described previously, then as illustrated in FIG. 13($a$) and FIG. 14($a$), the bevelled region 71 will appear white and the unbevelled region 72 will appear dark, thereby making it possible to distinguish between the two regions firstly by visual observation. The unbevelled region 72 does not go completely black like the background because even though it is called an unbevelled region 72, it is ground to some extent and bears some scratches. The distinction is not necessarily clear, and FIG. 13($a$), for instance, shows a degree of unevenness in the bevelling state compared to FIG. 14($a$).

Figure 14A:
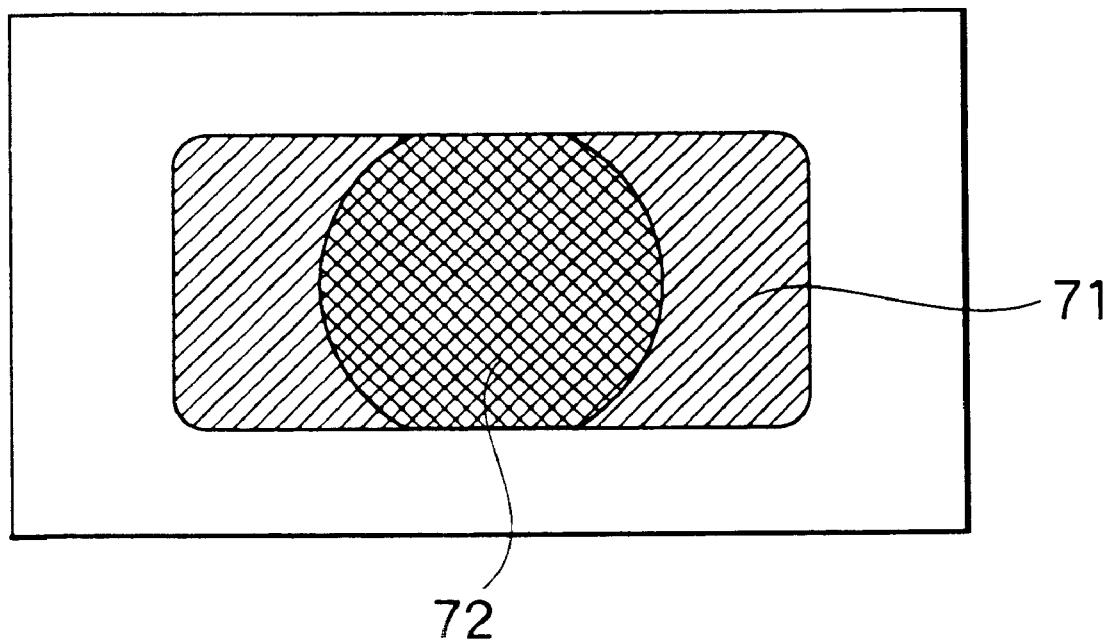
FIG. 14(a) is an image before digitization and FIG. 14(b) is a digitized image.
Figure 14B:
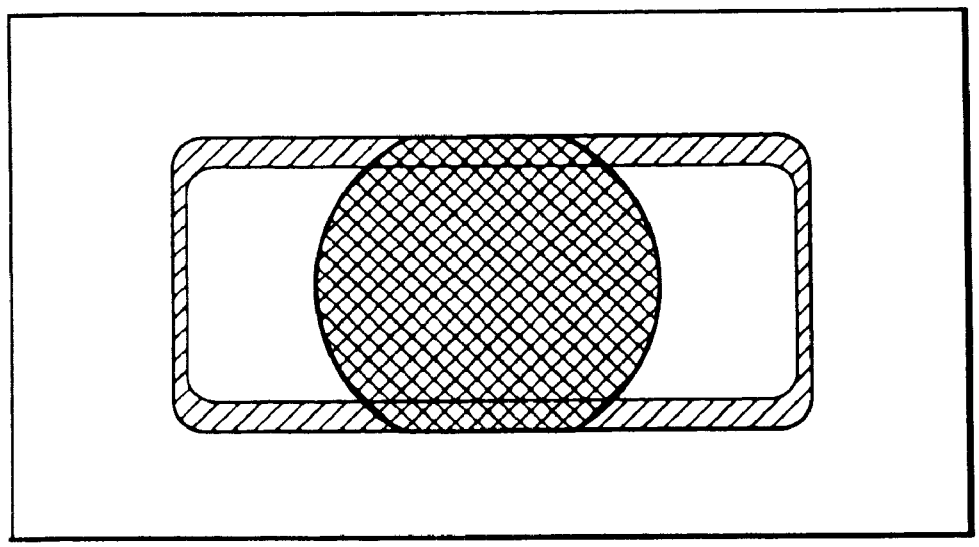

After taking an image whereby the bevelled region and unbevelled region can be distinguished, as in FIG. 13($a$) and FIG. 14($a$) (step 405), the image signal is digitized on the basis of a threshold value set automatically, such that the unbevelled region and bevelled region can be distinguished clearly by means of a two-stage light/dark gradation (steps 406~407). The threshold value used here is determined automatically for each crystal blank using a commonly known statistical method. As shown in FIG. 13($b$) and FIG. 14($b$), where the digital data is converted to an image, the unbevelled region 72 and bevelled region 71, which were not necessarily defined precisely in FIG. 13($a$) and FIG. 14($a$), are clearly distinguished by means of the two-stage light/dark gradation and are made to stand out. In FIG. 13($b$) and FIG. 14($b$), a portion of the outer perimeter is masked, for convenience.

Moreover, in order to obtain data for bevelling inspection, the digital data is subjected to statistical processing (step 408). There are various methods for statistical processing for inspecting bevelling on all sides of a blank, but here the following method was adapted. Namely, a straight line is drawn in a lateral direction over the image of a crystal blank having the shape of a thin ship, the data on the straight line is added up to produce an average value, which is taken as a series value, and series values are then gathered for the whole length of the object by shifting the straight line to parallel positions, a small pitch at a time. FIG. 15 and FIG. 16 give illustrations of the results gathered. FIG. 15 and FIG. 16 give a very good reflection of the corresponding results in FIG. 13($b$) and FIG. 14($b$), and they enable the variation in the bevelling state to be observed quantitatively (in FIG. 15, in particular, the rough state stands out markedly and the bevelling state is poor compared to FIG. 16.) In FIG. 15 and FIG. 16, the horizontal axis indicates the length of the crystal blank and the vertical axis represents the quantity of light.

Once bevelling inspection has been completed, the crystal blank 1 is sucked up again by the vacuum chuck 16 and conveyed to the next process by a conveyor robot arm 15. Here, since grooves 4 are formed on the mounting surface 3 of the mounting platform 2, a smooth pick-up operation and stable conveyance can be achieved, without the crystal blank 1 adhering to, and refusing to separate from, the mounting platform 2. In the subsequent process, GO/NO GO judgement can be made according to the bevelling inspection.

As described above, in the present embodiment, since small scratches produced in any direction on a blank surface by bevelling processing of a crystal blank can be emphasized and detected without creating any blind spots, a reliable distinction can be made between bevelled regions and unbevelled regions, and the bevelling state can be detected to a high degree of accuracy. Furthermore, since a plurality of bevelling states can be inspected and recognized instantly in real time by image processing, and data can also be obtained in large quantities by statistical processing, quality management for bevelling becomes possible and consequently, standardization of the bevelling process, and high reliability GO/NO GO judgement becomes possible.

Furthermore, since statistical methods are used, then even if there is variation in the bevelling process or the acid treatment carried out subsequently, the threshold value can be set for each crystal blank, and therefore flexible tolerances can be used and these tolerances can be set to the inspection standards, thereby eliminating cases where satisfactory products are taken as defective or defective products are taken as satisfactory. Furthermore, if the aforementioned bevelling inspection is carried out for both sides of the crystal blank rather than just one side, the reliability of quality judgement can be raised yet further.

An embodiment of an inspection method for a crystal substrate according to the present invention is now described with reference to the drawings.

Figure 20:
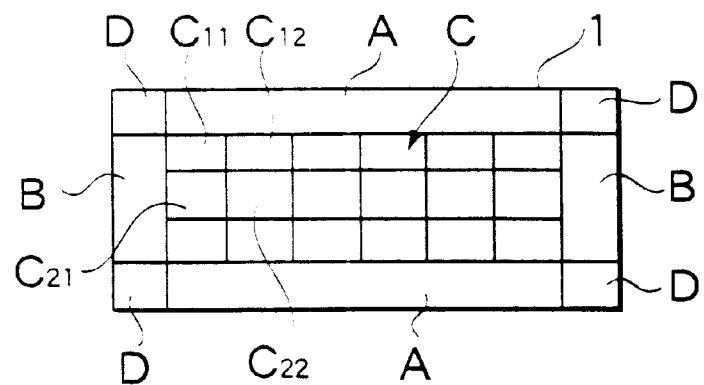
FIG. 20 is an illustrative diagram showing the division of regions in a crystal blank according to a further embodiment.
Figure 20:
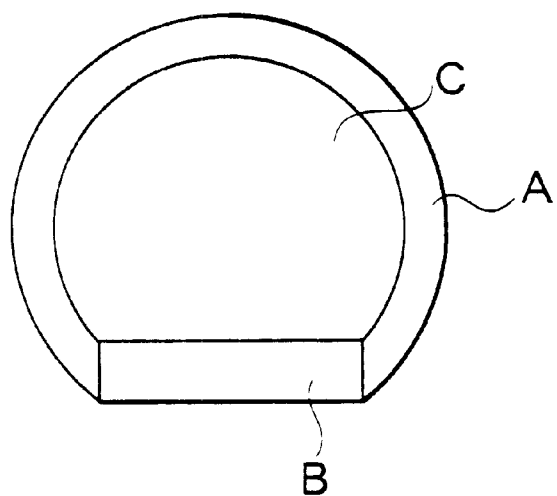
Figure 20:
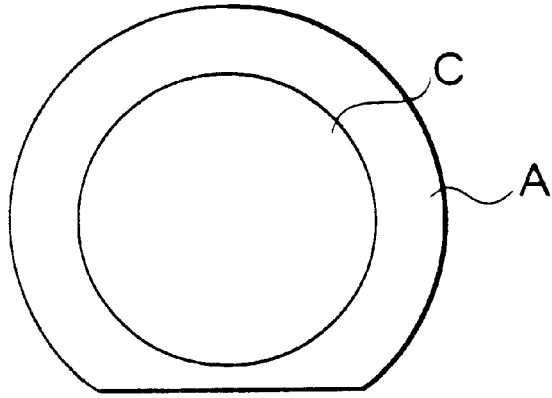
Figure 23:
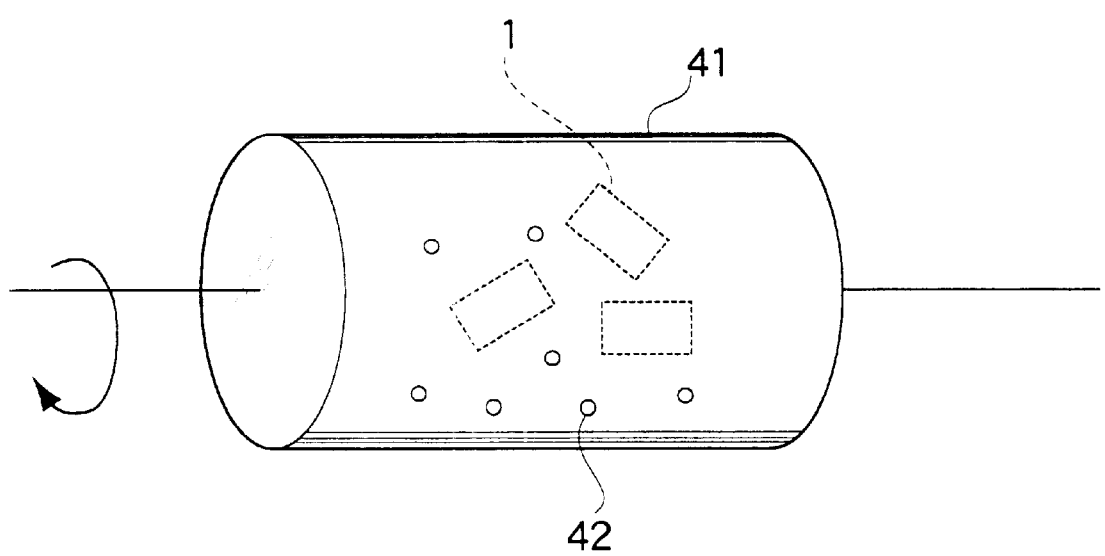
FIG. 23 is an illustrative diagram of a cylindrical barrel method for carrying out bevelling.
Figure 24:
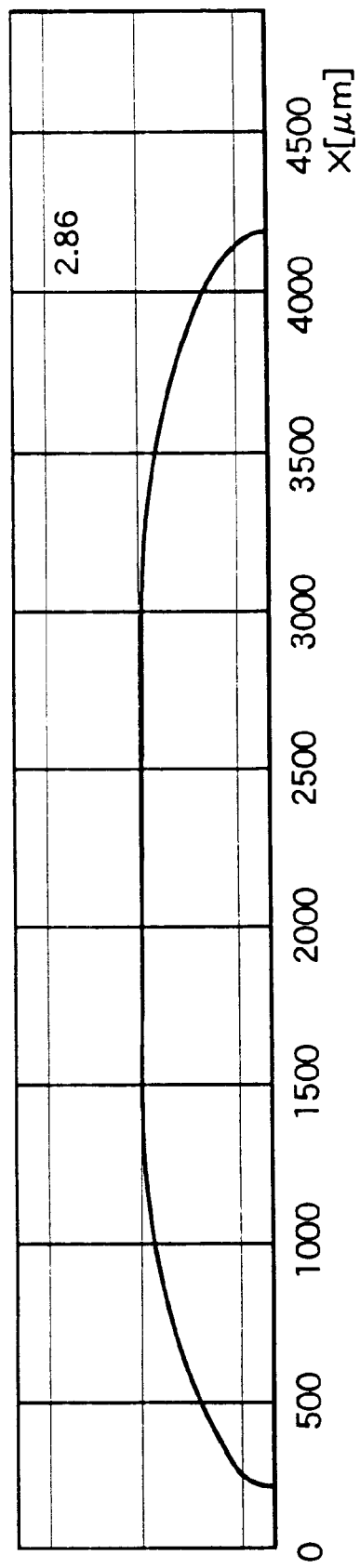
FIG. 24 is a characteristics graph plotting data obtained by a conventional level measurement method in the longitudinal direction of a crystal blank.

FIG. 20 is an image of a crystal blank actually being measured. For the sake of convenience, the white and black are shown reversed here, but since the background and crystal blank are in the dark field, they are black and the outline of the blank and scratches thereon show up white. Essentially, the ideal is that there should be no scratches whatsoever across the whole surface. Also, desirably, the outline should be rectangular. However it is impossible to achieve this ideal in practice, and as shown in FIG. 20, the items have corners missing, scratches along one edge or on the inner portion thereof, or the like. The aforementioned scratch inspection device is capable of identifying scratches and defects of this kind in images, and therefore it can be used to remove all items of this kind as defective items. However, of these, there are also scratches which do not pose any problems in terms of practical use. For example, depending on their location on the blank, it may be acceptable for a blank to have a number of scratches or defects. In order to save such blanks, when inspecting scratches on a crystal blank, it is necessary to divide the image of the blank surface of the crystal blank into a plurality of regions, set the required inspection standard independently for each region, and inspect each region according to the set inspection standard.

Figure 17:
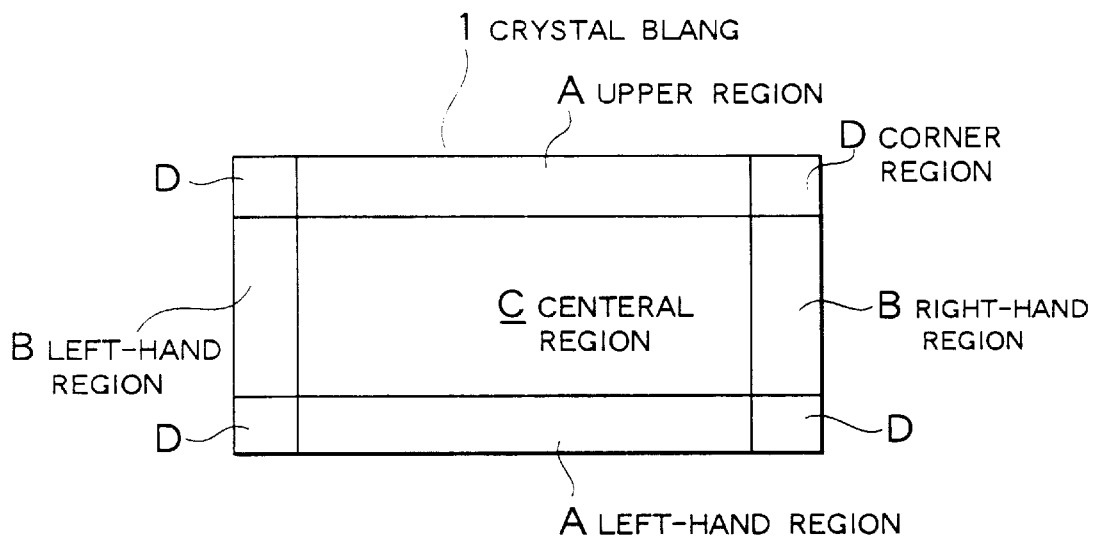
FIG. 17 is an illustrative diagram showing the division of regions in a crystal blank image according to an embodiment.
Figure 18:
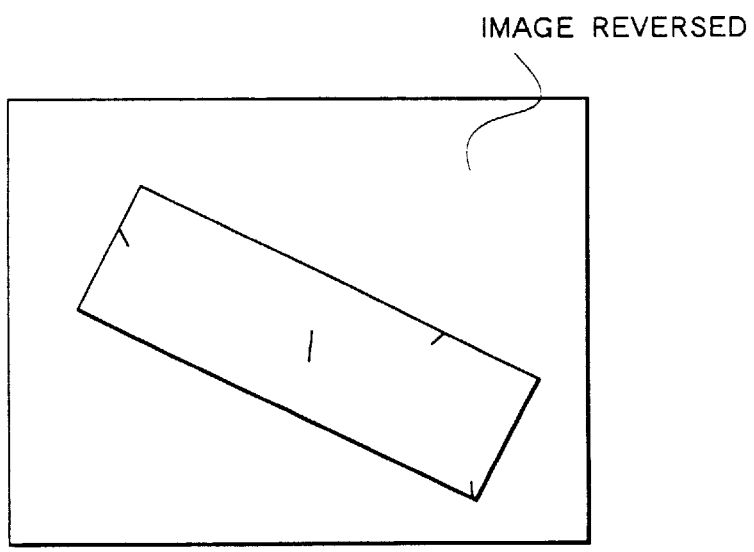
FIG. 18 is an illustrative diagram showing an actual crystal blank image according to an embodiment.

Therefore, in the present invention, the image of the thin strip-shaped crystal blank 1 is divided into a plurality of regions as shown in FIG. 17. Regions D are corner regions at the four corners of the blank; regions A are a pair of band-shaped upper and lower regions running in parallel to the upper and lower edges of the blank and taking the upper or lower edges as one of their edges, minus the corner regions D; regions B are a pair of band-shaped left and right-hand regions running in parallel to the left and right-hand edges of the blank and taking the right or left-hand edges as one of their edges, minus the corner regions D; and region C is a central region surrounded by regions A and regions B. Region C is mainly the area which functions as a crystal oscillator, so its inspection standards are most severe. Regions A include the longer edges, so they are next in order of severity. Regions B include the short edges, so they are lower in rank. And regions D are used for soldering, a number of scratches or defects here can be ignored.

This designation of regions is set by the personal computer 10 shown in FIG. 1 and supplied to the image processing device 14. A setting screen in the personal computer 10 for inspecting scratches in crystal blanks is now described with reference to FIG. 19.

Figure 19:
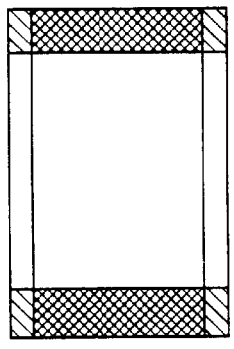
FIG. 19 is a diagram showing a personal computer setting screen for scratch inspection according to an embodiment.

Firstly, the parameter button on the toolbar displayed on the setting screen is selected. When this is selected, a screen like that shown in FIG. 19 is displayed, and as can be seen from the left half of the screen, the parameter file name (test1.PAR) is shown. An input button, save button, and print button are also provided, and by clicking on the input button, set values can be input, by clicking on the save button the set values can be saved, and by clicking on the print button, the setting contents can be printed out.

In the shape selection column, three round boxes are prepared: two, namely, ship and circular, indicating scratch inspection modes, and one, namely, bevel, indicating bevelling inspection mode. If a mark is entered in the strip, round box, then this indicates that the shape of the crystal blank which is to be inspected is a rectangular strip shape, and if a mark is entered in the circular round box, then this indicates that the crystal blank has a circular shape. If a mark is entered in the bevel round box, then this indicates the equipment is in bevel mode for inspecting the bevelling state, rather than scratch inspection. In the example illustrated, a mark is entered in the ship round box.

In the region A and B short edge dimensions column, there is an A box and a B box, and the length of the shorter edges of regions A is entered in box A, whilst the length of the shorter edges of regions B is entered in box B, in mm units. In the example shown, 0.020 (mm) is set in box A and 0.100 (mm) is set in box B.

The picture shown below the regions A and B shorter dimension column is an illustrative diagram of the regions into which the strip-shaped crystal blank is divided. At the bottom part of the screen, a parameter autoset button is provided and the parameters can be set automatically by clicking on this parameter autoset button.

Next, the light half of the screen is described. In the outer dimensions column are provided a longer edge box, a shorter edge box, a diagonal angle display, and an R (corner) box, and in the longer edge box, the standard size of the longer edge of the crystal blank and the relevant margin of tolerance are entered whilst in the shorter edge box, the standard size of the shorter edge and the relevant margin of tolerance are entered in mm units. The diagonal angle indicates the length of the diagonal line of the crystal blank, and it is provided in order to eliminate blanks which are not rectangular in shape, for example, diamond shapes, or shapes lacking lateral symmetry. If the long edge and the short edge of the blank are input, the diagonal angle is displayed by automatic calculation, so data can only be input to the tolerance margin box. The length of this diagonal line is a common standard which is investigated for a pair of diagonal lines. This item may also be stipulated in terms of the angles, rather than the diagonal line. In the R (corner) box, the standard shortest distance from an ideal perpendicular corner region to an actual corner region having a radius can be input in mm units, along with the relevant tolerance margin.

In the example illustrated, the aforementioned external dimensions are set as shown below.

| | |
|---|---|
| Longer edge | 6.000 ± 0.012 (mm) |
| Shorter edge | 1.800 ± 0.020 (mm) |
| Diagonal | 1.800 ± 0.0141 (mm) |
| R (corner) | 0.050 ± 0.030 (mm) |

The shape of a crystal blank under investigation is inspected by means of these external dimension settings, and if the dimensions are within the tolerances, then the item is satisfactory, and if they exceed the tolerances, then the item is defective.

In the measurement level and scratch surface area column, there are: an A (long edge) level and A scratch surface area box; a B (short edge) level and B scratch surface area box; a C (internal) level and C scratch surface area box; a D (four corner) level and D scratch surface area box; and a C (internal) stain and C stain surface area box; and settings can be entered in each box. Here, a stain refers to dirt, oil film, or the like, adhering to the surface of the crystal blank. The different levels indicate the threshold value (any unit) of image brightness for digitization of the input image, and the surface area values indicate the smallest surface area (any unit) which can be judged as a scratch in each region. Therefore, if the image read in by the image capturing device is above the set level and above the set scratch surface area, then it is judged first to contain a scratch, but if it is above the set level but below the set scratch surface area, or above the set scratch surface area but below the set level, then it is not judged to contain a scratch. Various types of dispersion can be expressed by 256 gradations using 8 bits, and the relevant settings can be entered into the A box, B box and C box provided. The requirements relating to these dispersion settings are added as a further AND condition to the AND condition of the aforementioned level and scratch surface area.

Here, the aforementioned measurement level and scratch surface area are set as given below.

| A (long edge) level | 150 | A scratch surface area | 5 |
| B (short edge) level | 150 | B scratch surface area | 5 |
| C (internal) level | 100 | C scratch surface area | 10 |
| D (four corners) level | 200 | D scratch surface area | 5 |
| C (internal) stain | 30 | C stain surface area | 40 |
| Dispersion A 100 | B 150 | C 80 | |

Regions where there is no scratching on the crystal blank are projected as a dark image, whilst scratch regions are projected as light. Therefore, the purpose of having setting levels for each region individually is in order that a darker (stricter) threshold value is set for the C region where stricter standards are required, whilst a lighter (less strict) threshold value is set for the D regions where the standard is more relaxed. Furthermore, compared to the other regions, the scratch surface area of the C region is set relatively large in relation to the setting level. Moreover, there is a significant difference between the C region stain settings and scratch settings, namely, the stain level is set lower than the scratch level, since the emphasis of the light is lower, and the stain surface area is set larger than the scratch surface area, since the broadening is greater. The standards relating to dispersion are also stricter for the C region.

Scratches in the crystal blanks under inspection are classified according to this measurement level, scratch surface area and dispersion, and if the values obtained are within the tolerances, then it is regarded that there is no scratching, and if they exceed the tolerances, then it is regarded that there is a scratch.

At the bottom of the right-hand side, there are provided a parameter input button (F8) and an end button (F10), and parameters can be input or the inspection setting process can be ended by clicking on these buttons.

In the aforementioned embodiment, the crystal blank is divided into four types of region, A~D, but the present invention is not limited to this. For example, the scratch distribution trends in unprocessed regions can be examined by dividing the central region C further into a plurality of regions or chessboard-type squares (C11, C12 . . .), as in FIG. 20(*a*). Moreover, if the crystal blank is circular, then it may be divided into a number of regions according to requirements, for instance, a perimeter region A, central region C, and border region B, as shown in FIG. 20(*b*), or simply a perimeter region A and central region C, as shown in FIG. 20(*c*).

In bevelling inspection, the crystal blank 1 is divided into a plurality of regions A~D, as shown in FIG. 17, the inspection standard required is set for each region, A~D, and each region is inspected according to the corresponding set inspection standard.

The standards for the left and right-hand regions B may be more lenient. Since the corner regions D are more liable to contain defects and do not form a part of the crystal oscillator, the corresponding standards may also be relaxed, similarly to the left and right-hand regions. The upper and lower regions A contribute to device characteristics, so their standards are more severe. Furthermore, in the central region C, it is required that there should be no bevelling, so the standards in this region are more severe, similar to the upper and lower regions A. As shown in FIG. 21, bevelling inspection standards are set in the foregoing manner on a personal computer screen. At the same time, shape selection, dimensions, and the like, relating to the crystal blank under inspection are input. The set values and the input values are transmitted to the image processing device and image processing is carried out on the basis of these.

ADVANTAGES OF THE INVENTION

In this way, according to the present invention, since indentations such as grooves, holes, or the like, are formed on the flat mounting surface of a mounting platform, there is no sliding of the crystal substrate over the mounting platform during mounting, and the mounting position on the mounting platform is stable. Furthermore, the crystal substrate does not adhere tightly to the mounting platform, and it can be conveyed smoothly during pick-up. Therefore, increased speed in scratch inspection, and the like, relating to crystal substrates can be achieved.

Moreover, according to the present invention, since images can be identified objectively by emphasizing bevelled regions in a dark field of illumination, the operability of bevelling inspection is raised dramatically and standardization of bevelling inspection can be achieved.

According to the method of the present invention, since the distinction between bevelled regions and unbevelled regions is made clear by digitization the input image, bevelling inspection is made even easier and excellent inspection reliability is achieved.

According to the method of the present invention, the whole surface of a substrate can be inspected and a large number of substrates can be checked in a short period of time. Moreover, the inspection data can be fed back to the bevelling technology, and the bevelling process and inspection can be standardization.

According to the present invention, the bevelling state can be inspected instantly by a single image capturing device. Furthermore, since indentations, such as grooves, holes, and the like, are formed in the flat mounting surface of a mounting platform, there is no sliding of the crystal substrate over the mounting platform during mounting, and the mounting position on the mounting platform is stable. Furthermore, the crystal substrate does not adhere tightly to the mounting platform, and it can be conveyed smoothly during pick-up. Therefore, increased speed in scratch inspection, and the like, relating to crystal substrates can be achieved.

According to the present invention, since on-line processing is possible, rapid, high-volume bevelling inspection can be carried out in real time, and objective inspection data is obtained. Furthermore, inspection data can be fed back to the bevelling technology, thereby enabling improvements in bevelling technology to be achieved. Consequently, the characteristics of the crystal substrates are improved and productivity is also improved.

If illumination means is provided below the crystal substrate, as in the present invention, then it does not become an obstacle when the crystal substrate is moved, and a smooth inspection operation can be implemented.

Preferably, light-emitting diodes should be used as the aforementioned illumination means, as in the present invention. The lifespan of light-emitting diodes is markedly longer than conventional illumination sources, such as halogen lamps, or the like. Furthermore, the amount of heat generated is lower, making handling easier. Moreover, the light-emitting diodes may produce concentrated or diffused light. Stable measurement cannot be achieved if irregularities occur in the light shined onto the crystal substrate, but by providing a plurality of reflecting plates, such as mirrors, surrounding the diodes, it is possible to shine a uniform light onto the crystal substrate, and diffusing plates do not need to be used in conjunction with the light source.

Moreover, according to the present invention, accurate inspection can be achieved by means of inspection standards which correspond to regions. According to the second claim of the present invention, since accurate inspection corresponding to particular regions can be achieved, and inspection data containing information relating to regions can be obtained, then standardization of inspection and analysis control become simpler to achieve. Furthermore, according to the present invention, practicable scratch inspection can be implemented. According to the present invention, practicable bevelling inspection can also be implemented.

What is claimed is:

1. A mounting platform for mounting transparent substrates, in a substrate processing section for carrying out prescribed processes with respect to transparent substrates conveyed in and out by a conveying mechanism, said mounting platform is made from a transparent material, and indentations, such as grooves, holes, or the like, are formed in a flat mounting surface on which said transparent substrates are mounted.

2. The mounting platform for transparent substrates according to claim 1, wherein sapphire is used as the transparent material for said mounting platform.

3. The mounting platform for transparent substrates according to claim 2, wherein the boundary regions between the flat mounting surface and the indentations in said mounting platform are formed such that they are smoothly connected.

4. A scratch inspection device for transparent substrates whereby scratches are detected on the basis of an image signal of a transparent substrate captured by shining light onto the transparent substrate, comprising:

a mounting platform made from a transparent material, wherein indentations, such as grooves, holes, or the like, are formed in a flat mounting surface on which a transparent substrate is mounted horizontally;

illumination means for shining scattered light, diffused within an illumination angle of ±30° in a vertical direction with respect to the horizontal substrate face of the transparent substrate, from all sides of the perimeter of the transparent substrate; and image capturing means for capturing an image of a transparent substrate from a vertical direction with respect to the substrate face of the transparent substrate.

5. The scratch inspection device for transparent substrates according to claim 4, wherein the aforementioned illumination means is provided below the transparent substrate.

6. The scratch inspection device for transparent substrates according to claim 5, wherein light-emitting diodes are used as said illumination means.

7. The scratch inspection device for transparent substrates according to claim 6, wherein said transparent substrates are crystal blanks for crystal oscillators.

8. A bevelling inspection method for transparent substrates, comprising the steps of:

shining scattered light, diffused within an illumination angle of ±30° in a vertical direction with respect to the horizontal substrate face of a transparent substrate, from all sides of the perimeter of the transparent substrate;

capturing an image of the transparent substrate from a perpendicular direction to the substrate surface of the illuminated transparent substrate; and reading in the captured image of the substrate surface of the transparent substrate, and carrying out a bevelling inspection from the image read in.

9. The bevelling inspection method for transparent substrates according to claim 8, wherein a bevelling inspection is carried out by digitizing the image read in.

10. The bevelling inspection method for transparent substrates according to claim 9, wherein said digitized data is subjected to statistical processing and a bevelling inspection is carried out from the processing results.

11. The bevelling inspection method for transparent substrates according to claim 10, wherein said transparent substrates are crystal blanks for crystal oscillators.

12. A bevelling inspection device for transparent substrates, whereby a bevelling inspection is carried out on the basis of an image signal of a transparent substrate captured by shining light onto a transparent substrate which has undergone bevelling, comprising:

a mounting platform made from a transparent material, wherein indentations, such as grooves, holes, or the like, are formed in a flat mounting surface on which a transparent substrate is mounted horizontally;

illumination means for shining scattered light, diffused within an illumination angle of ±30° in a vertical direction with respect to the horizontal substrate face of a transparent substrate, from all sides of the perimeter of the transparent substrate; and image capturing means for capturing an image of the transparent substrate from a perpendicular direction to the substrate surface of the transparent substrate.

13. A bevelling inspection device for transparent substrates, comprising:

a substrate supplying device for supplying transparent substrates;

a conveyor robot for conveying transparent substrates supplied by the substrate supplying device to a mounting platform;

a mounting platform made from a transparent material, wherein indentations, such as grooves, holes, or the like, are formed in a flat mounting surface on which a transparent substrate conveyed by the conveyor robot is mounted horizontally;

illumination means for shining scattered light, diffused within an illumination angle of ±30° in a vertical direction with respect to the horizontal substrate face of a transparent substrate mounted on the mounting platform, from all sides of the perimeter of the transparent substrate;

image capturing means for capturing an image of the transparent substrate from a perpendicular direction to the substrate surface of the transparent substrate illuminated by the illumination means; and an image processing device for extracting scratches caused by bevelling present on the transparent substrate, from an image signal captured by the image capturing means, and carrying out statistical processing on the basis of the extracted signal.

14. The bevelling inspection device for transparent substrates according to claim 13, wherein said transparent substrates are crystal blanks for crystal oscillators.

15. An inspection method for transparent substrates comprising the steps of:

dividing an image of the substrate surface of a transparent substrate into a plurality of regions when inspecting a transparent substrate;

setting inspection standards required for said regions individually for each of said regions; and inspecting each region in accordance with the set inspection standards.

16. The inspection method according to claim 15, wherein, in cases where said transparent substrates are thin strip-shaped substrates, the image of said substrate surface is divided into Ocorner regions at the four corners of the substrate a pair of band-shaped upper and lower regions running parallel to the upper and lower edges of the substrate, minus said corner regions, and taking the upper or lower edge as one of their edges; a pair of band-shaped left and right-hand regions running parallel to the left and right-hand edges of the substrate, similarly minus said corners regions, and taking the left or right-hand edge as one of their edges; and a central region surrounded by the upper and lower regions and the left and right-hand regions.

17. The inspection method for transparent substrates according to claim 16, wherein said inspection is scratch inspection.

18. The inspection method for transparent substrates according to claim 16, wherein said inspection is bevelling inspection.

19. The inspection method for transparent substrates according to claim 16, wherein said transparent substrates are crystal blanks for crystal oscillators.

* * * * *

UNITED STATES PATENT AND TRADEMARK OFFICE
CERTIFICATE OF CORRECTION

PATENT NO. : 6,256,091 B1
DATED : July 3, 2001
INVENTOR(S) : Ryo Kobayashi

It is certified that error appears in the above-identified patent and that said Letters Patent is hereby corrected as shown below:

Claim 16,
Line 4, change "into Ocorner" to -- into: corner --; and
Line 5, change "substrate a pair of" to -- substrate; a pair of --.

Signed and Sealed this

Sixteenth Day of April, 2002

Attest:

Attesting Officer

JAMES E. ROGAN
Director of the United States Patent and Trademark Office